(12) United States Patent
Tachibana et al.

(10) Patent No.: US 6,624,335 B2
(45) Date of Patent: Sep. 23, 2003

(54) ETHER, POLYMER, RESIST COMPOSITION AND PATTERNING PROCESS

(75) Inventors: Seiichiro Tachibana, Nakakubiki-gun (JP); Mutsuo Nakashima, Nakakubiki-gun (JP); Tsunehiro Nishi, Nakakubiki-gun (JP)

(73) Assignee: Shin Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/046,264

(22) Filed: Jan. 16, 2002

(65) Prior Publication Data

US 2002/0161150 A1 Oct. 31, 2002

(30) Foreign Application Priority Data

Jan. 17, 2001 (JP) ........................ 2001-008988

(51) Int. Cl.[7] .............................................. C07C 41/00
(52) U.S. Cl. ................. 568/664; 568/579; 568/667; 526/258; 526/266; 526/271; 526/282; 526/319; 526/332
(58) Field of Search .................. 568/579, 664, 568/667; 526/258, 266, 271, 282, 319, 332

(56) References Cited

PUBLICATIONS

Del Valle et al. Tetrahedron (1995), 51(30), 8259–78.*
Oda et al. Tetrahedron (1995), 51 (3), 695–702.*
Horton et al. Carbohydrate Research (1993), 250(2), 261–74.*
Buchbauer et al. Monatshefte fur Chemie (1983), 114(11), 1237–46.*

* cited by examiner

Primary Examiner—Helen L. Pezzuto
(74) Attorney, Agent, or Firm—Millen White Zelano & Branigan, P.C.

(57) ABSTRACT

An ether compound of formula (1) is provided wherein $R^1$ is H or $C_{1-6}$ alkyl, $R^2$ is $C_{1-6}$ alkyl, $R^3$ is H, $C_{1-15}$ acyl or $C_{1-15}$ alkoxycarbonyl which may be substituted with halogen atoms, k is 0 or 1, m is from 0 to 3, and n is from 3 to 6. The ether compound is polymerized to form a polymer having improved reactivity, robustness and substrate adhesion. A resist composition comprising the polymer as a base resin is sensitive to high-energy radiation, has excellent sensitivity, resolution, and etching resistance, and lends itself to micropatterning with electron beams or deep-UV

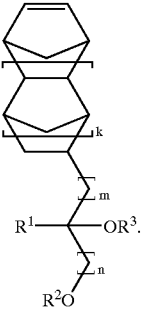

(1)

4 Claims, No Drawings

ETHER, POLYMER, RESIST COMPOSITION AND PATTERNING PROCESS

This invention relates to (i) an ether compound, (ii) a polymer comprising specific recurring units, (iii) a resist composition comprising the polymer as a base resin, and (iv) a patterning process using the resist composition.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

For resist materials for use with a KrF excimer lasers, polyhydroxystyrene having a practical level of transmittance and etching resistance is, in fact, a standard base resin. For resist materials for use with ArF excimer lasers, polyacrylic or polymethacrylic acid derivatives and polymers containing aliphatic cyclic compounds in the backbone are under investigation. All these polymers have advantages and disadvantages, and none of them have been established as the standard base resin.

More particularly, resist compositions using derivatives of polyacrylic or polymethacrylic acid have the advantages of high reactivity of acid-decomposable groups and good substrate adhesion and give relatively satisfactory results with respect to sensitivity and resolution, but have extremely low etching resistance and are impractical because the resin backbone is weak. On the other hand, resist compositions using polymers containing alicyclic compounds in their backbone have a practically acceptable level of etching resistance because the resin backbone is robust, but are very low in sensitivity and resolution because the reactivity of acid-decomposable protective groups is extremely low as compared with those on the acrylic polymers. Since the backbone of the resin is too robust, substrate adhesion is poor. These compositions are thus impractical as well. While a finer pattern rule is being demanded, there is a need to have a resist material which is satisfactory in sensitivity, resolution, and etching resistance.

SUMMARY OF THE INVENTION

Therefore, an object of the present invention is to provide (i) an ether compound capable of forming a polymer having improved substrate adhesion, (ii) a polymer having improved reactivity, robustness and substrate adhesion, (iii) a resist composition comprising the polymer as a base resin, which has a higher resolution and etching resistance than conventional resist compositions, and (iv) a patterning process using the resist composition.

It has been found that novel ether compounds of formula (1) below which are produced by the method to be described later can form polymers having improved substrate adhesion, and that novel polymers obtained therefrom and having a weight average molecular weight of 1,000 to 500,000 have improved reactivity, robustness or rigidity and substrate adhesion; that a resist composition comprising the polymer as the base resin has a high resolution and etching resistance; and that this resist composition lends itself to precise micropatterning.

In a first aspect, the invention provides an ether compound of the following general formula (1).

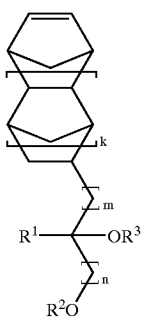

(1)

Herein $R^1$ is hydrogen or a straight, branched or cyclic alkyl group of 1 to 6 carbon atoms, $R^2$ is a straight, branched or cyclic alkyl group of 1 to 6 carbon atoms, $R^3$ is hydrogen or an acyl or alkoxycarbonyl group of 1 to 15 carbon atoms in which some or all of the hydrogen atoms on the constituent carbon atoms may be substituted with halogen atoms, k is 0 or 1, m is an integer from 0 to 3, and n is an integer from 3 to 6.

In a second aspect, the invention provides a polymer comprising recurring units of the following general formula (1-1) or (1-2) derived from the ether compound of the above formula (1) and having a weight average molecular weight of 1,000 to 500,000.

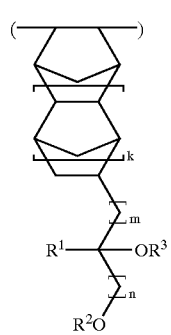

(1-1)

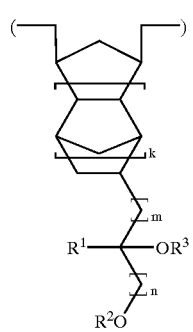

(1-2)

Herein k, m, n, and $R^1$ to $R^3$ are as defined above.

In one preferred embodiment, the polymer contains, in addition to the recurring units of formula (1-1), recurring units of the following general formula (2-1).

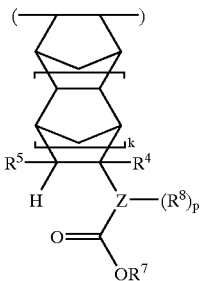

(2-1)

Herein k is as defined above; $R^4$ is hydrogen, methyl or $CH_2CO_2R^6$; $R^5$ is hydrogen, methyl or $CO_2R^6$; $R^6$ is a straight, branched or cyclic alkyl group of 1 to 15 carbon atoms; $R^7$ is an acid labile group; $R^8$ is selected from the class consisting of a halogen atom, a hydroxyl group, a straight, branched or cyclic alkoxy, acyloxy or alkylsulfonyloxy group of 1 to 15 carbon atoms, and a straight, branched or cyclic alkoxycarbonyloxy or alkoxyalkoxy group of 2 to 15 carbon atoms, in which some or all of the hydrogen atoms on constituent carbon atoms may be substituted with halogen atoms; Z is a single bond or a straight, branched or cyclic (p+2)-valent hydrocarbon group of 1 to 5 carbon atoms, in which at least one methylene may be substituted with oxygen to form a chain-like or cyclic ether or two hydrogen atoms on a common carbon may be substituted with oxygen to form a ketone; and p is 0, 1 or 2.

In another preferred embodiment, the polymer contains, in addition to the recurring units of formula (1-1), recurring units of the following general formulae (2-1) and (3).

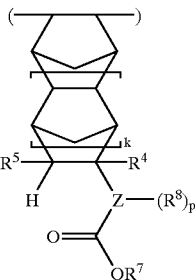

(2-1)

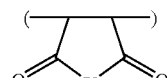

(3)

Herein Z, k, p and $R^4$ to $R^8$ are as defined above, and Y is an oxygen atom or $NR^9$ wherein $R^9$ is a straight, branched or cyclic alkyl group of 1 to 6 carbon atoms.

In a further preferred embodiment, the polymer contains, in addition to the recurring units of formula (1-1), recurring units of the following general formula (4) alone or in combination with recurring units of the following general formula (2-1), and recurring units of the following general formula (3).

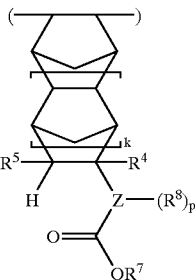

(2-1)

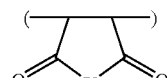

(3)

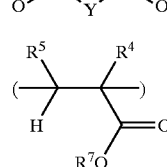

(4)

Herein Y, Z, k, p and $R^4$ to $R^9$ are as defined above.

In a still further preferred embodiment, the polymer contains, in addition to the recurring units of formula (1-2), recurring units of the following general formula (2-2).

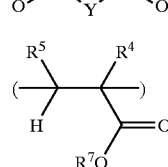

(2-2)

Herein Z, k, p and $R^4$ to $R^8$ are as defined above.

In a third aspect, the invention provides a resist composition comprising the polymer defined above.

In a fourth aspect, the invention provides a process for forming a resist pattern comprising the steps of applying the resist composition onto a substrate to form a coating; heat treating the coating and then exposing it to high-energy radiation or electron beams through a photo mask; and optionally heat treating the exposed coating and developing it with a developer.

The ether compounds of formula (1) are highly polar due to the inclusion of a hydroxyl, acyloxy or alkoxycarbonyloxy group as well as an ether structure. The polymers comprising recurring units of formula (1-1) or (1-2) derived from the ether compounds thus exhibit improved substrate adhesion. The polymers also have high rigidity since bridged aliphatic rings are incorporated in the backbone. A carbon chain of an appropriate length introduced between the ether structure and the rigid backbone serves to properly alleviate the rigidity which has been excessive in the prior art. Since the ether structure moiety is spaced apart from the backbone, it can act more positively as a polar group. These factors cooperate to develop a substrate adhesion force surpassing the prior art compositions. Although low reactivity is left outstanding in the prior art, the carbon chain introduced allows the acid generated to diffuse, thereby improving reactivity and as an accompanying benefit, achieving a reduction of line edge roughness. Therefore, a resist composition using the polymer as a base resin satisfies all the performance factors of sensitivity, resolution and etch resistance and is very useful in forming micropatterns.

DESCRIPTION OF THE PREFERRED EMBODIMENTS

Ether

The ether compound of the invention has the following general formula (1).

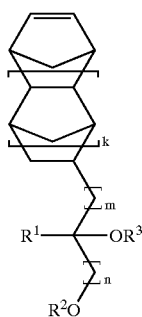

Herein $R^1$ is hydrogen or a straight, branched or cyclic alkyl group of 1 to 6 carbon atoms. Exemplary alkyl groups include methyl, ethyl, n-propyl, isopropyl, n-butyl, isobutyl, sec-butyl, tert-butyl, tert-amyl, n-pentyl, n-hexyl, cyclopentyl, and cyclohexyl. $R^2$ is a straight, branched or cyclic alkyl group of 1 to 6 carbon atoms, examples of which are the same as exemplified for $R^1$. $R^3$ is hydrogen or an acyl or alkoxycarbonyl group of 1 to 15 carbon atoms in which some or all of the hydrogen atoms on the constituent carbon atoms may be substituted with halogen atoms. Exemplary of $R^3$ are formyl, acetyl, propionyl, pivaloyl, methoxycarbonyl, ethoxycarbonyl, tert-butoxycarbonyl, trifluoroacetyl, trichloroacetyl, and 3,3,3-trifluoropropionyl. The letter k is 0 or 1, m is an integer from 0 to 3, and n is an integer from 3 to 6.

Illustrative, non-limiting, examples of the ether compound of formula (1) are given below. In the formulae below and throughout the specification, Ac is acetyl and t-Bu is tert-butyl.

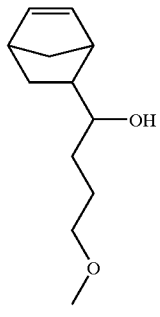 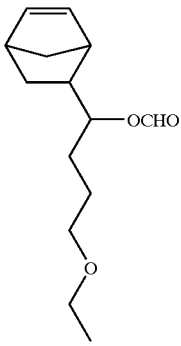

-continued

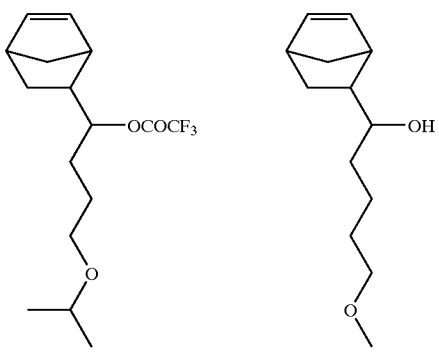

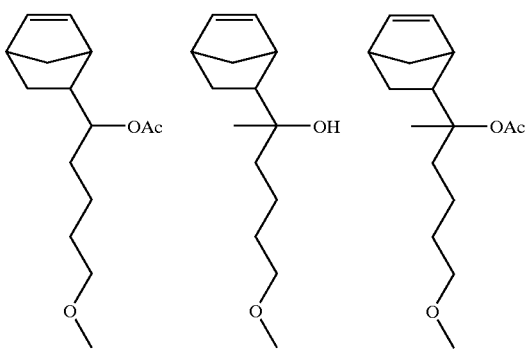

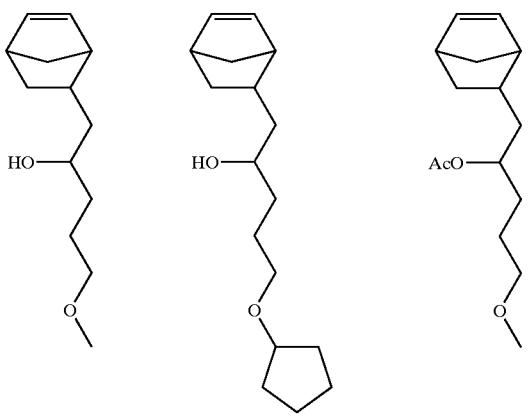

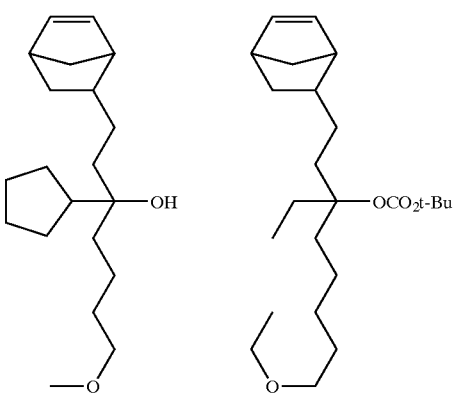

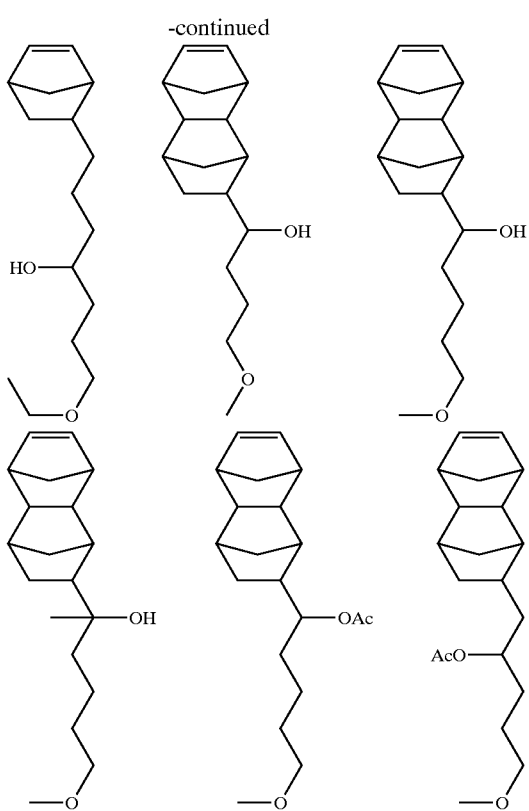

The ether compound of the invention can be prepared according to the following reaction scheme, but the invention is not limited thereto.

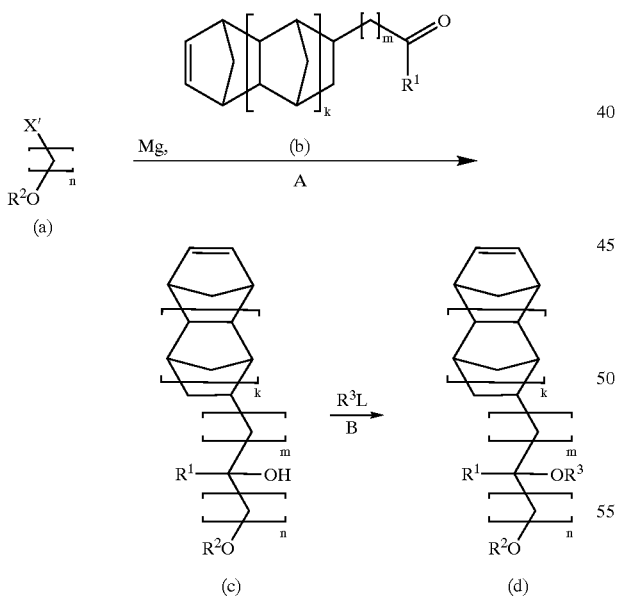

Herein, k, m, n, and $R^1$ to $R^3$ are as defined above, X' is a halogen atom, and L is an eliminatable group such as hydroxyl, halogen, acyloxy, alkoxycarbonyloxy or p-nitrophenyloxy group.

Step A is to subject a carbonyl compound (b) to nucleophilic addition reaction using a Grignard reagent prepared from a halogenated ether (a) and magnesium, thereby forming an alcohol (c). Grignard reaction is referred to as a typical example of nucleophilic addition reaction, but this step is not limited thereto. The reaction readily takes place under well-known conditions although it is preferred to mix the reactants, halogenated ether (a), carbonyl compound (b) and magnesium in a solvent such as tetrahydrofuran or diethyl ether, while heating or cooling the reaction solution if necessary.

Step B is to esterify the alcohol (c) into a corresponding acyl or alkoxycarbonyl compound (d). The esterifying agents $R^3L$ used herein include carboxylic acids (where L=OH) such as formic acid, acid halides (where L=halogen) such as acetyl chloride, acetyl bromide and propionyl chloride, acid anhydrides (where L=acyloxy or alkoxycarbonyloxy) such as acetic anhydride, trifluoroacetic anhydride, mixed acid anhydride of formic acid/acetic acid, and di-t-butyl dicarbonate, and activated esters (where L=an eliminatable group such as p-nitrophenyloxy) such as p-nitrophenyl acetate and p-nitrophenyl propionate. Except the case where the esterifying agent is carboxylic acid, it is desired to use a base such as triethylamine, pyridine and 4-dimethylaminopyridine. The reaction readily takes place under well-known conditions although it is preferred to mix the reactants, alcohol (c), esterifying agent $R^3L$ and optionally, the base in a solventless system or in a solvent such as tetrahydrofuran, diethyl ether, n-hexane or toluene, while heating or cooling the reaction solution if necessary.

Polymer

The polymers or high molecular weight compounds according to the invention are characterized by comprising recurring units of the following general formula (1-1) or (1-2) derived from the ether compound of formula (1) and having a weight average molecular weight of 1,000 to 500,000.

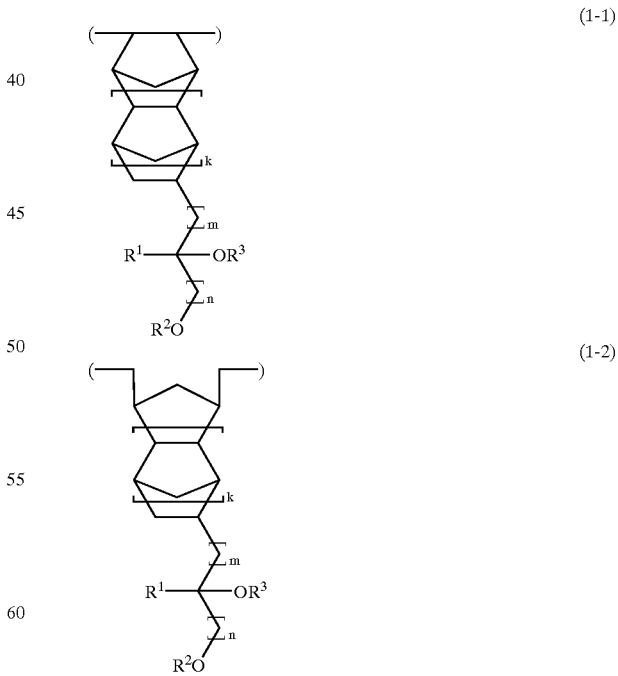

Herein k, m, n and $R^1$ to $R^3$ are as defined above.

More specifically, the polymers of the invention are divided into the following four subgenuses of polymers.

Subgenus (I) includes polymers comprising, in addition to the recurring units of formula (1-1), recurring units of the following general formula (2-1).

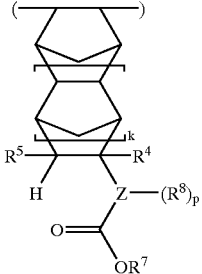

(2-1)

Herein k is as defined above; $R^4$ is hydrogen, methyl or $CH_2CO_2R^6$; $R^5$ is hydrogen, methyl or $CO_2R^6$; $R^6$ is a straight, branched or cyclic alkyl group of 1 to 15 carbon atoms; $R^7$ is an acid labile group; $R^8$ is selected from the class consisting of a halogen atom, a hydroxyl group, a straight, branched or cyclic alkoxy, acyloxy or alkylsulfonyloxy group of 1 to 15 carbon atoms, and a straight, branched or cyclic alkoxycarbonyloxy or alkoxyalkoxy group of 2 to 15 carbon atoms, in which some or all of the hydrogen atoms on constituent carbon atoms may be substituted with halogen atoms; Z is a single bond or a straight, branched or cyclic (p+2)-valent hydrocarbon group of 1 to 5 carbon atoms, in which at least one methylene may be substituted with oxygen to form a chain-like or cyclic ether or two hydrogen atoms on a common carbon may be substituted with oxygen to form a ketone; and p is 0, 1 or 2.

Subgenus (II) includes polymers comprising, in addition to the recurring units of formula (1-1), recurring units of the following general formulae (2-1) and (3).

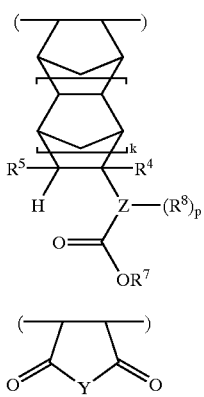

(2-1)

(3)

Herein Z, k, p and $R^4$ to $R^8$ are as defined above. Y is an oxygen atom or $NR^9$ wherein $R^9$ is a straight, branched or cyclic alkyl group of 1 to 6 carbon atoms. Examples of $R^9$ include methyl, ethyl, n-propyl, isopropyl, n-butyl, isobutyl, sec-butyl, tert-butyl, tert-amyl, n-pentyl, n-hexyl, cyclopentyl and cyclohexyl.

Subgenus (III) includes polymers comprising, in addition to the recurring units of formula (1-1), recurring units of the following general formula (4) alone or in combination with recurring units of the following general formula (2-1), and recurring units of the following general formula (3).

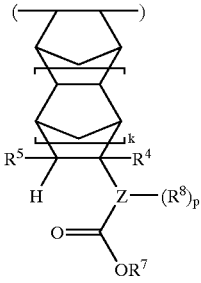

(2-1)

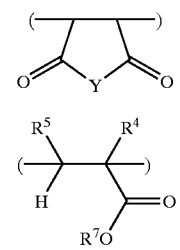

(3)

(4)

Herein Y, Z, k, p and $R^4$ to $R^9$ are as defined above.

Subgenus (IV) includes polymers comprising, in addition to the recurring units of formula (1-2), recurring units of the following general formula (2-2).

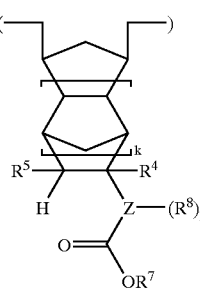

(2-2)

Herein Z, k, p and $R^4$ to $R^8$ are as defined above.

More particularly, $R^4$ is hydrogen, methyl or $CH_2CO_2R^6$. $R^5$ is hydrogen, methyl or $CO_2R^6$. $R^6$ stands for straight, branched or cyclic alkyl groups of 1 to 15 carbon atoms, such as, for example, methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl and butyladamantyl. $R^7$ stands for acid labile groups to be described later.

$R^8$ is selected from among a halogen atom, a hydroxyl group, a straight, branched or cyclic alkoxy, acyloxy or alkylsulfonyloxy group of 1 to 15 carbon atoms, and a straight, branched or cyclic alkoxycarbonyloxy or alkoxyalkoxy group of 2 to 15 carbon atoms, in which some or all of the hydrogen atoms on constituent carbon atoms may be substituted with halogen atoms. Exemplary of $R^8$ are fluoro, chloro, bromo, methoxy, ethoxy, n-propoxy, isopropoxy, n-butoxy, sec-butoxy, tert-butoxy, tert-amyloxy, n-pentoxy, n-hexyloxy, cyclopentyloxy, cyclohexyloxy, ethylcyclopentyloxy, butylcyclopentyloxy, ethylcyclohexyloxy, butylcyclohexyloxy, adamantyloxy, ethyladamantyloxy, butyladamantyloxy, formyloxy, acetoxy, ethylcarbonyloxy, pivaloyloxy, methoxycarbonyloxy, ethoxycarbonyloxy, tert-butoxycarbonyloxy, methanesulfonyloxy, ethanesulfonyloxy, n-butanesulfonyloxy, trifluoroacetoxy, trichloroacetoxy, 2,2,2-trifluoroethylcarbonyloxy, methoxymethoxy, 1-ethoxyethoxy, 1-ethoxypropoxy, 1-tert-butoxyethoxy, 1-cyclohexyloxyethoxy, 2-tetrahydrofuranyloxy, and 2-tetrahydropyranyloxy.

Z is a single bond or a straight, branched or cyclic (p+2)-valent hydrocarbon group of 1 to 5 carbon atoms, in which at least one methylene may be substituted with oxygen to form a chain-like or cyclic ether or two hydrogen atoms on a common carbon may be substituted with oxygen to form a ketone. In case of p=0, for example, exemplary Z groups are methylene, ethylene, trimethylene, tetramethylene, pentamethylene, hexamethylene, 1,2-propanediyl, 1,3-butanediyl, 1-oxo-2-oxapropane-1,3-diyl, 3-methyl-1-oxo-2-oxabutane-1,4-diyl. In case of p≠0, exemplary Z groups are (p+2)-valent groups obtained by eliminating one or two hydrogen atoms from the above-exemplified groups.

The acid labile groups represented by $R^7$ may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

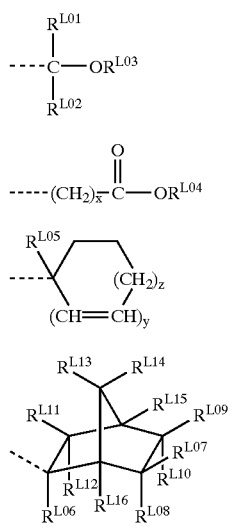

In these formulae and throughout the specification, the broken line denotes a free valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, and n-octyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like. Illus trative examples are the substituted alkyl groups shown below.

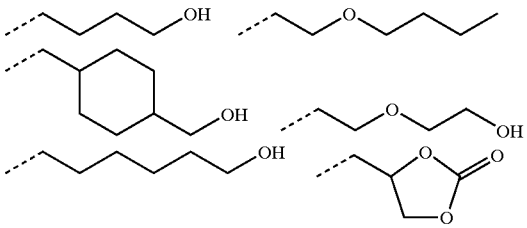

A pair of $R^{L01}$ and $R^{L02}$, $R^{L01}$ and $R^{L03}$, or $R^{L02}$ and $R^{L03}$ may form a ring. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter x is an integer of 0 to 6.

$R^{L05}$ is a monovalent hydrocarbon group of 1 to 8 carbon atoms which may contain a hetero atom or a substituted or unsubstituted aryl group of 6 to 20 carbon atoms. Examples of the monovalent hydrocarbon group which may contain a hetero atom include straight, branched or cyclic alkyl groups such as methyl, ethyl, propyl, isopropyl, n-butyl, sec-butyl, tert-butyl, tert-amyl, n-pentyl, n-hexyl, cyclopentyl, and cyclohexyl, and substituted groups in which some hydrogen atoms on the foregoing groups are substituted with hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter y is equal to 0 or 1, z is equal to 0, 1, 2 or 3, and 2y+z is equal to 2 or 3.

$R^{L06}$ is a monovalent hydrocarbon group of 1 to 8 carbon atoms which may contain a hetero atom or a substituted or unsubstituted aryl group of 6 to 20 carbon atoms. Examples of these groups are the same as exemplified for $R^{L05}$.

$R^{L07}$ to $R^{L16}$ independently represent hydrogen or monovalent hydrocarbon groups of 1 to 15 carbon atoms which may contain a hetero atom. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted ones of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$–$C_{15}$ hydrocarbon group which may contain a hetero atom, when they form a ring, examples of which are the ones exemplified above for the monovalent hydrocarbon groups, with one hydrogen atom being eliminated. Two of $R^{L07}$ to $R^{L16}$ which are attached to adjoining carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

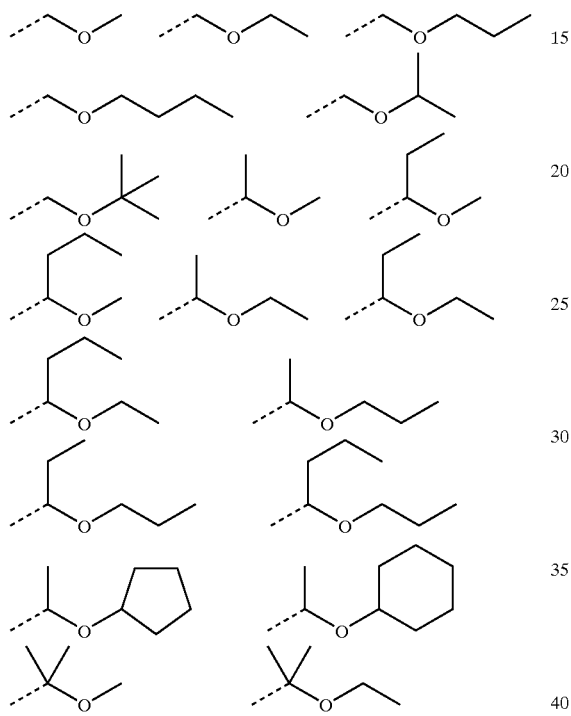

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonyl-methyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

The acid labile groups of formula (L4) are exemplified by the following groups.

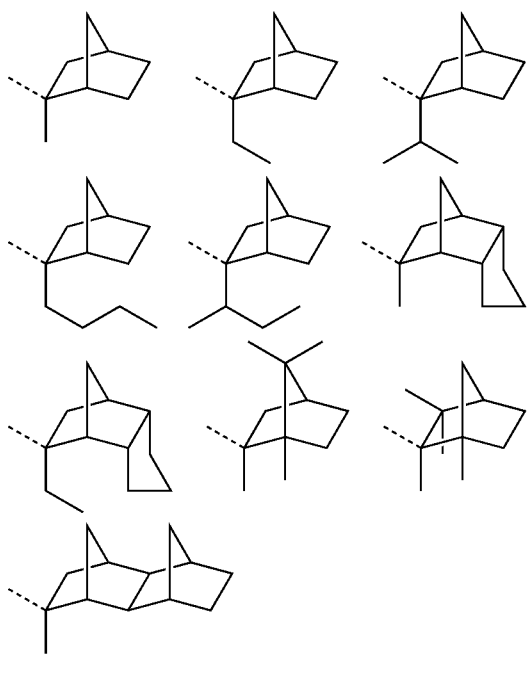

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

Illustrative, non-limiting, examples of the recurring units of formula (1-1) are given below.

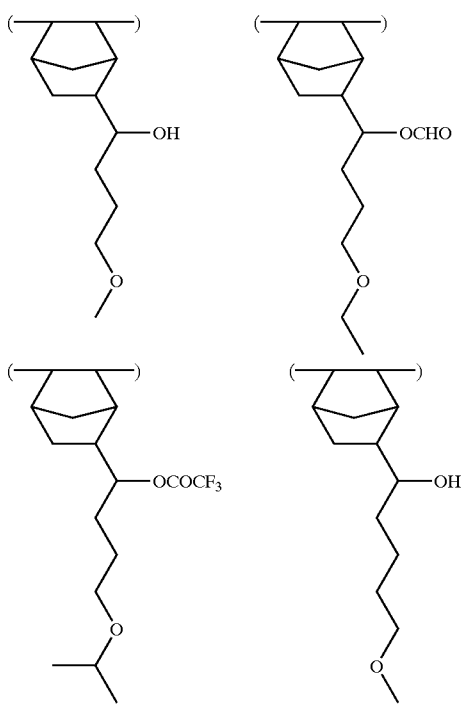

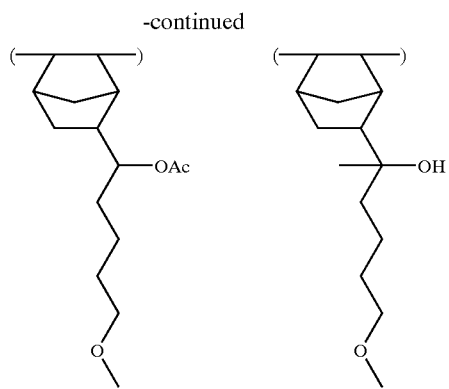
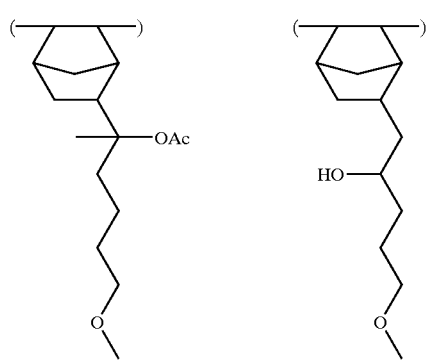
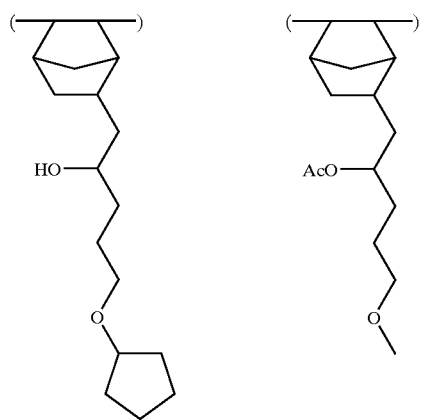
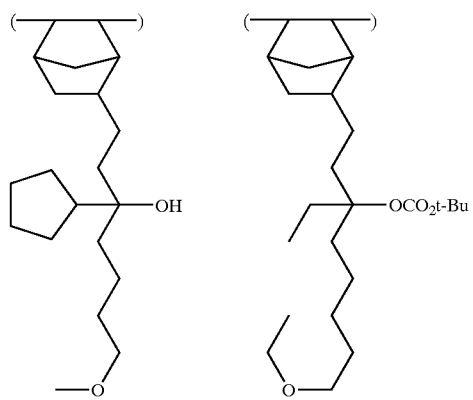
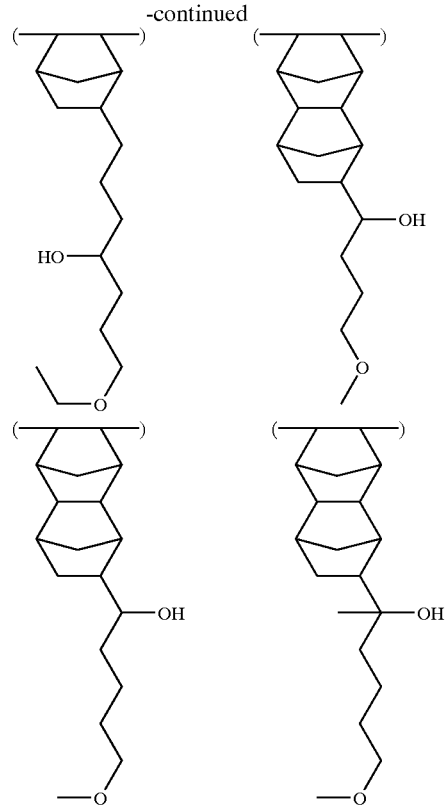
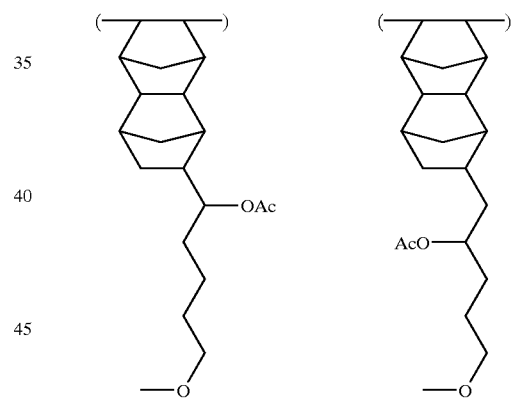
Illustrative, non-limiting, examples of the recurring units of formula (1-2) are given below.
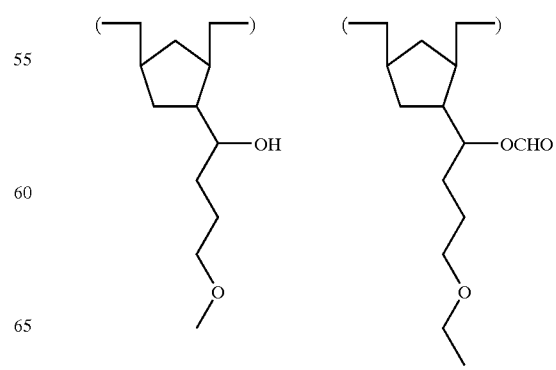

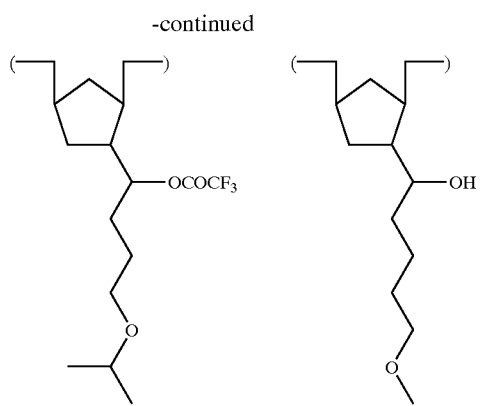
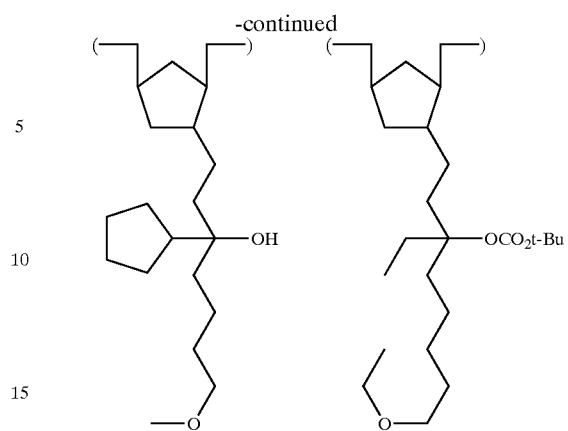
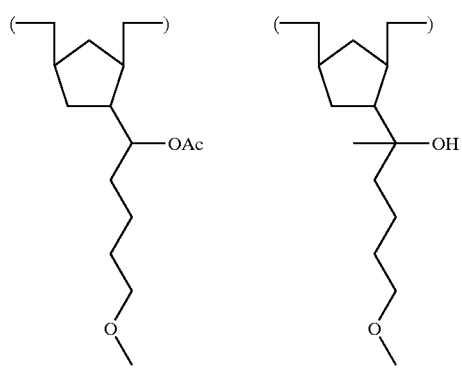
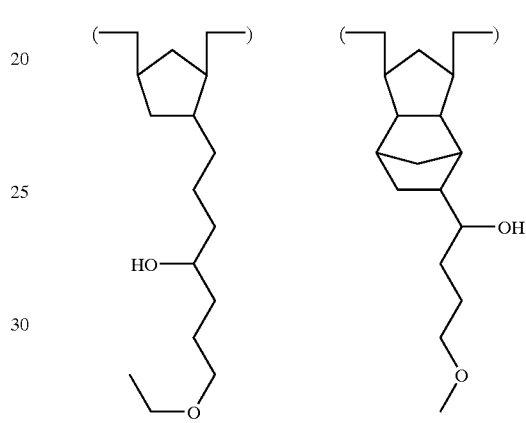
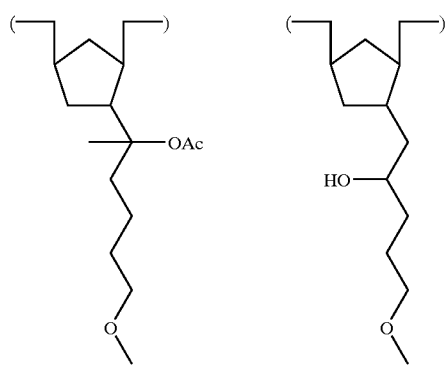
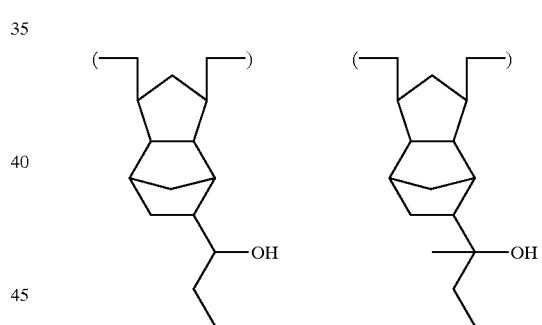
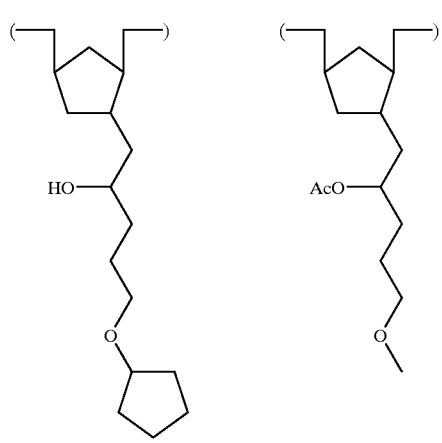
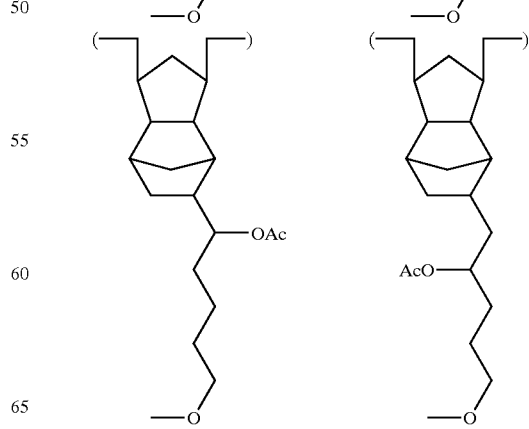

Illustrative, non-limiting, examples of the recurring units of formula (2-1) are given below.
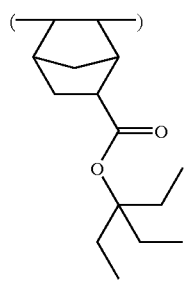
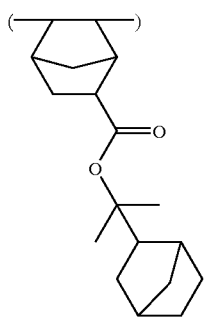
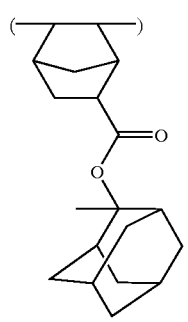
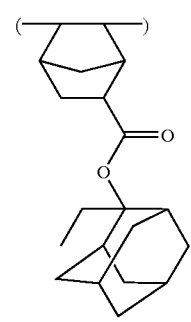
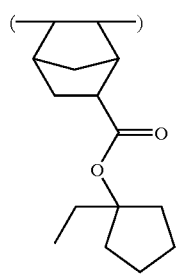
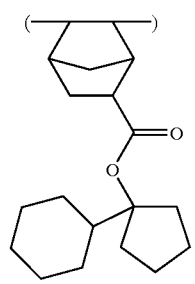
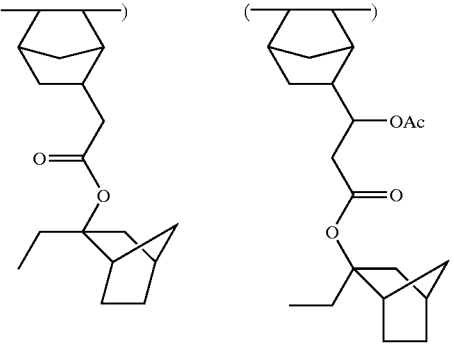
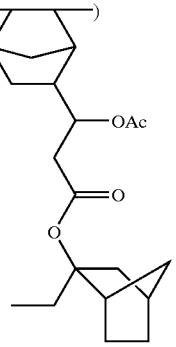
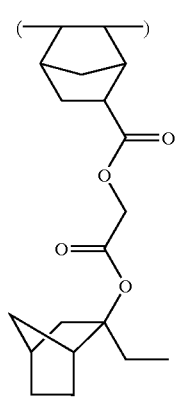
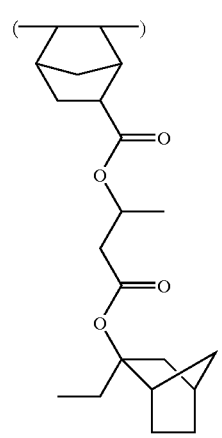
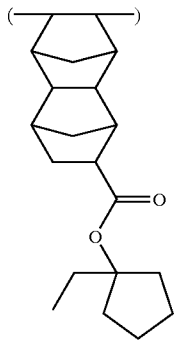
Illustrative, non-limiting, examples of the recurring units of formula (2-2) are given below.
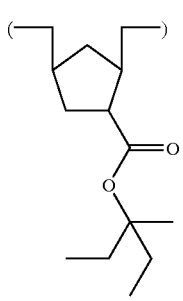
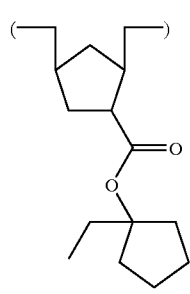

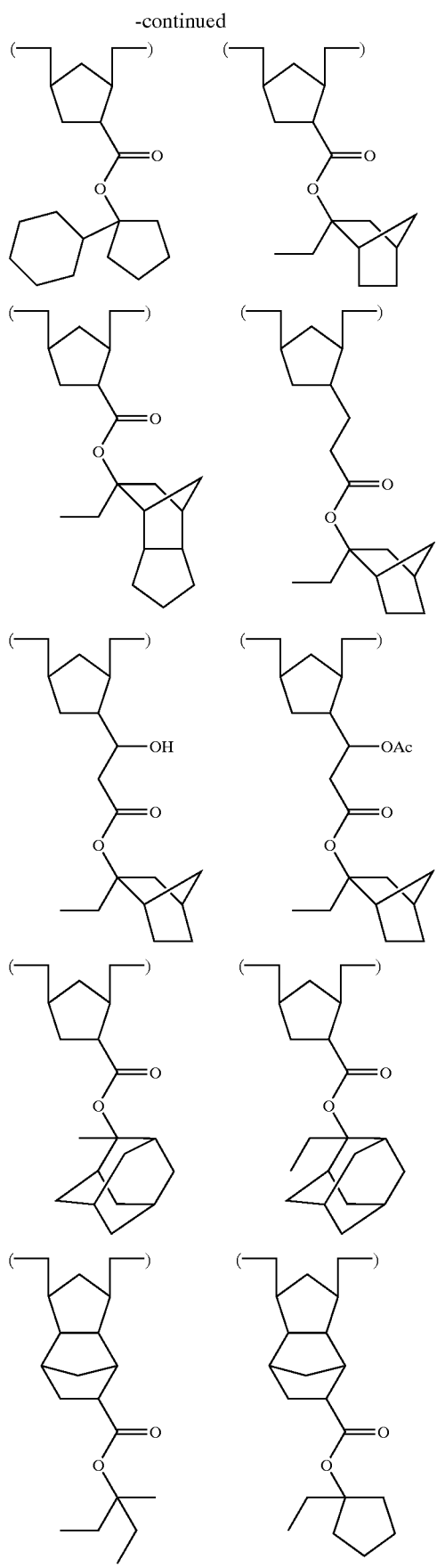
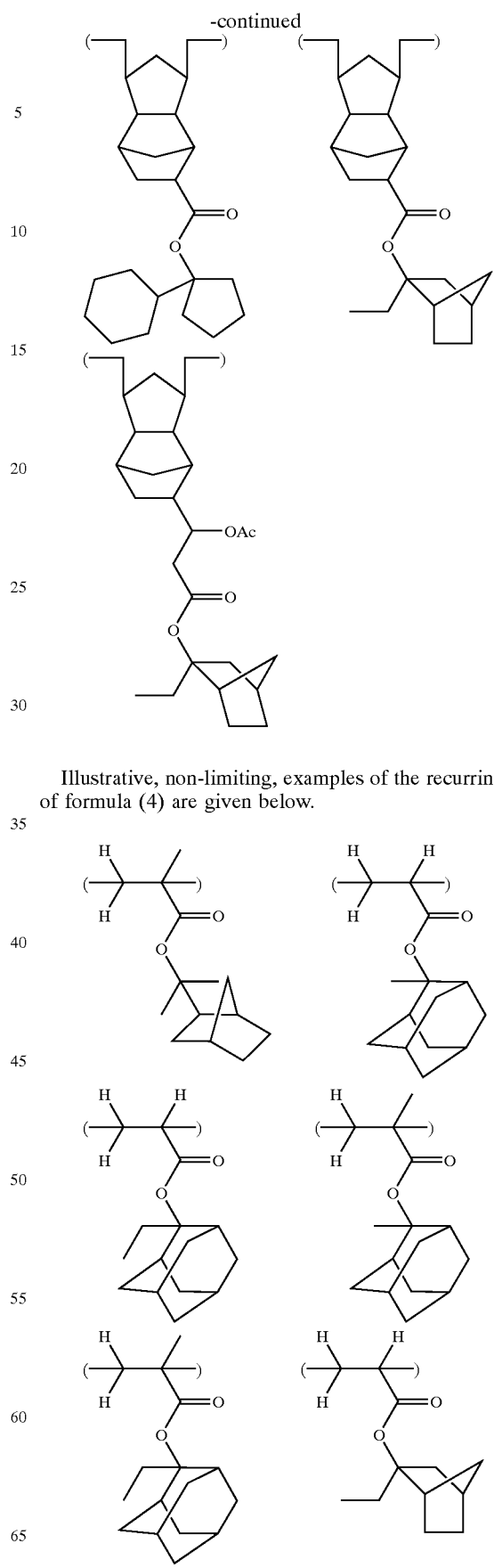
Illustrative, non-limiting, examples of the recurring units of formula (4) are given below.

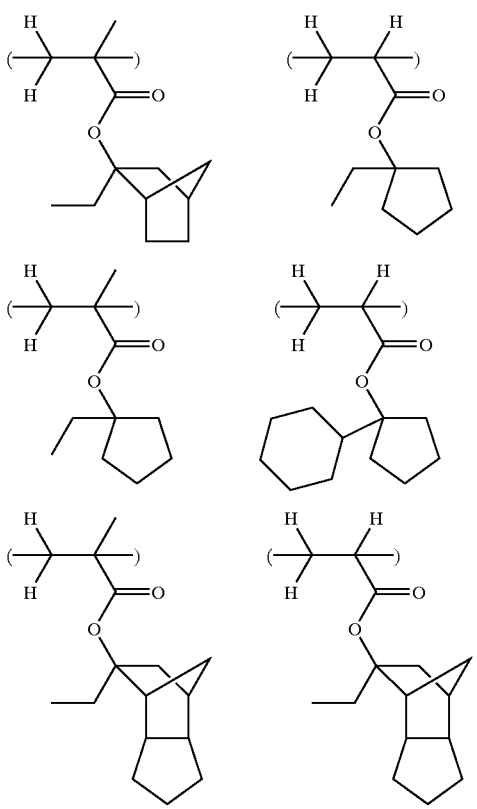
If desired, the polymers of the invention may further contain recurring units of one or more types selected from units of the following general formulae (M1) to (M8-2).
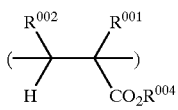 (M1)
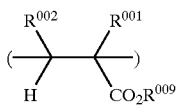 (M2)
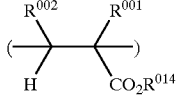 (M3)
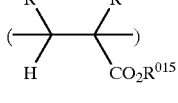 (M4)
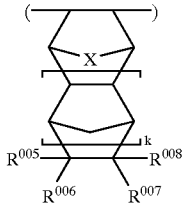 (M5-1)
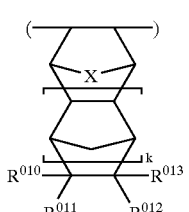 (M6-1)
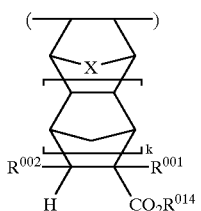 (M7-1)
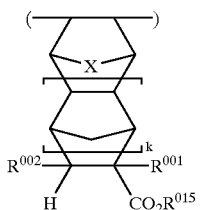 (M8-1)
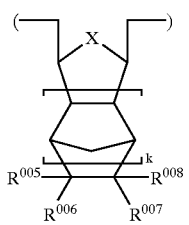 (M5-2)
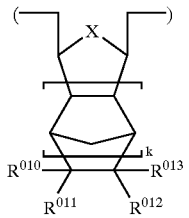 (M6-2)
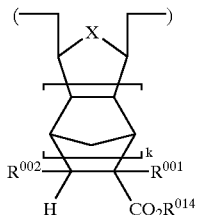 (M7-2)
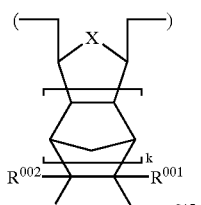 (M8-2)
Herein, $R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms. $R^{004}$ is hydrogen or a monovalent hydrocarbon group of 1 to 15 carbon atoms having a carboxyl or hydroxyl group. At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. $R^{009}$ is a monovalent hydrocarbon group of 3 to 15 carbon atoms containing a —$CO_2$— partial structure. At least one of $R^{010}$ to $R^{013}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. $R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently single bonds or straight, branched or cyclic alkylene groups of 1 to 15 carbon atoms. $R^{014}$ is a polycyclic hydrocarbon group having 7 to 15 carbon atoms or an alkyl group containing a polycyclic hydrocarbon group. $R^{015}$ is an acid labile group. X is $CH_2$ or an oxygen atom. Letter k is equal to 0 or 1.

More illustratively, $R^{003}$ is a straight, branched or cyclic alkyl group of 1 to 15 carbon atoms, for example, methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl.

$R^{004}$ is hydrogen or a monovalent hydrocarbon group of 1 to 15 carbon atoms having a carboxyl or hydroxyl group, for example, carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, and hydroxyadamantyl.

At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Examples of the carboxyl or hydroxyl-bearing monovalent hydrocarbon group of 1 to 15 carbon atoms include carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, and hydroxyadamantyloxycarbonyl. Examples of the straight, branched or cyclic alkyl group of 1 to 15 carbon atoms are the same as exemplified for $R^{003}$.

Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. Examples of the carboxyl or hydroxyl-bearing divalent hydrocarbon group of 1 to 15 carbon atoms include the groups exemplified as the carboxyl or hydroxyl-bearing monovalent hydrocarbon group, with one hydrogen atom eliminated therefrom. Examples of the straight, branched or cyclic alkylene groups of 1 to 15 carbon atoms include the groups exemplified for $R^{003}$, with one hydrogen atom eliminated therefrom.

$R^{009}$ is a monovalent hydrocarbon group of 3 to 15 carbon atoms containing a —$CO_2$— partial structure, for example, 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl.

At least one of $R^{010}$ to $R^{013}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. Examples of the monovalent hydrocarbon group of 2 to 15 carbon atoms containing a —$CO_2$— partial structure include 2-oxooxolan-3-yloxycarbonyl, 4,4-dimethyl-2-oxooxolan-3-yloxycarbonyl, 4-methyl-2-oxooxan-4-yloxycarbonyl, 2-oxo-1,3-dioxolan-4-ylmethyloxycarbonyl, and 5-methyl-2-oxooxolan-5-yloxycarbonyl. Examples of the straight, branched or cyclic alkyl groups of 1 to 15 carbon atoms are the same as exemplified for $R^{003}$.

$R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently single bonds or straight, branched or cyclic alkylene groups of 1 to 15 carbon atoms. Examples of the divalent hydrocarbon group of 1 to 15 carbon atoms containing a —$CO_2$— partial structure include 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl, as well as the groups exemplified as the monovalent hydrocarbon group containing a —$CO_2$— partial structure, with one hydrogen atom eliminated therefrom. Examples of the straight, branched or cyclic alkylene groups of 1 to 15 carbon atoms include the groups exemplified for $R^{003}$, with one hydrogen atom eliminated therefrom.

$R^{014}$ is a polycyclic hydrocarbon group having 7 to 15 carbon atoms or an alkyl group containing a polycyclic hydrocarbon group, for example, norbornyl, bicyclo[3.3.1]nonyl, tricyclo[5.2.1.0$^{2,6}$]decyl, adamantyl, ethyladamantyl, butyladamantyl, norbornylmethyl, and adamantylmethyl.

$R^{015}$ is an acid labile group, examples of which are the same as described above. X is $CH_2$ or an oxygen atom. Letter k is equal to 0 or 1.

The recurring units of formulae (M1) to (M8-2) are effective for imparting such desired properties as developer affinity, substrate adhesion and etching resistance to a resist composition based on a polymer comprising these recurring units. By adjusting the content of these recurring units, the performance of the resist composition can be finely adjusted.

The polymers of the invention have a weight average molecular weight of about 1,000 to 500,000, preferably about 3,000 to 100,000. Outside the range, the etching resistance may become extremely low and the resolution may become low because a substantial difference in rate of dissolution before and after exposure is lost.

The polymer of the invention can be prepared through copolymerization reaction using a compound of the follow ing general formula (1a) as a first monomer, one, two or three members selected from compounds of the following general formulae (2a) to (4a) as second to fourth monomers, and optionally, one or more members selected from compounds of the following general formulae (M1a) to (M8a) as subsequent monomers.

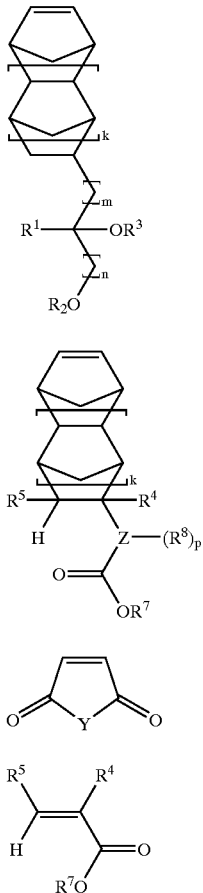

Herein, Y, Z, k, p, m, n, $R^1$ to $R^9$ are as defined above.

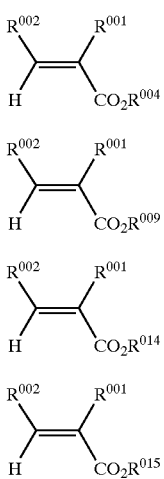

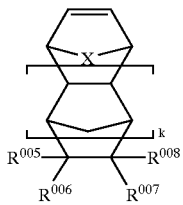

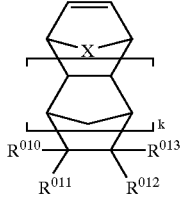

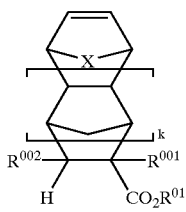

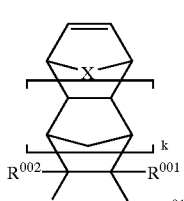

Herein, k, $R^{001}$ to $R^{015}$, and X are as defined above.

By properly adjusting the proportion of the respective monomers used in the copolymerization reaction, the polymer can be tailored so that it may exert the preferred performance when blended in resist compositions.

In addition to (i) the monomer of formula (1a), (ii) the monomer or monomers of formulas (2a) to (4a), and (iii) the monomer or monomers of formulae (M1a) to (M8a), the polymer of the invention may have copolymerized therewith (iv) another monomer having a carbon-to-carbon double bond other than (i) to (iii). Examples of the additional monomer (iv) include substituted acrylic acid esters such as methyl methacrylate, methyl crotonate, dimethyl maleate, and dimethyl itaconate, unsaturated carboxylic acids such as maleic acid, fumaric acid and itaconic acid, substituted or unsubstituted norbornenes such as norbornene and methyl norbornene-5-carboxylate, and unsaturated acid anhydrides such as itaconic anhydride.

In the polymers of the invention, the preferred proportion of recurring units based on the respective monomers is in the following range (in mol %), though not limited thereto.

(I) When the polymer is comprised of recurring units of formula (1-1) and recurring units of formula (2-1), it contains (i) 1 to 90%, preferably 5 to 80%, and more preferably 10 to 70% of recurring units of formula (1-1) based on the monomer of formula (1a), (ii) 1 to 90%, preferably 5 to 80%, and more preferably 10 to 70% of recurring units of formula (2-1) based on the monomer of formula (2a), (iii) 0 to 50%, preferably 0 to 40%, and more preferably 0 to 30% of recurring units of formula (M5-1) to (M8-1) based on the monomers of formula (M5a) to (M8a), and (iv) 0 to 50%, preferably 0 to 40%, and more preferably 0 to 30% of recurring units based on another monomer.

(II) When the polymer is comprised of recurring units of formula (1-1), recurring units of formula (2-1) and recurring units of formula (3), it contains (i) 1 to 49%, preferably 3 to 45%, and more preferably 5 to 40% of recurring units of formula (1-1) based on the monomer of formula (1a), (ii) 1 to 49%, preferably 3 to 45%, and more preferably 5 to 40% of recurring units of formula (2-1) based on the monomer of formula (2a), (iii) 50% of recurring units of formula (3) based on the monomer of formula (3a), (iv) 0 to 25%, preferably 0 to 20%, and more preferably 0 to 15% of recurring units of formula (M5-1) to (M8-1) based on the monomers of formula (M5a) to (M8a), and (v) 0 to 25%, preferably 0 to 20%, and more preferably 0 to 15% of recurring units based on another monomer.

(III) When the polymer is comprised of recurring units of formula (1-1), recurring units of formula (4) alone or in combination with recurring units of formula (2-1), and recurring units of formula (3), it contains (i) 1 to 49%, preferably 3 to 45%, and more preferably 5 to 40% of recurring units of formula (1-1) based on the monomer of formula (1a), (ii) 0 to 40%, preferably 0 to 35%, and more preferably 0 to 30% of recurring units of formula (2-1) based on the monomer of formula (2a), (iii) 1 to 80%, preferably 1 to 70%, and more preferably 1 to 50% of recurring units of formula (4) based on the monomer of formula (4a), (iv) 1 to 49%, preferably 5 to 45%, and more preferably 10 to 40% of recurring units of formula (3) based on the monomer of formula (3a), (v) 0 to 25%, preferably 0 to 20%, and more preferably 0 to 15% of recurring units of formula (M1a) to (M8-1) based on the monomers of formula (M1a) to (M8a), and (vi) 0 to 25%, preferably 0 to 20%, and more preferably 0 to 15% of recurring units based on another monomer.

(IV) When the polymer is comprised of recurring units of formula (1-2) and recurring units of formula (2-2), it contains (i) 1 to 90%, preferably 5 to 80%, and more preferably 10 to 70% of recurring units of formula (1-2) based on the monomer of formula (1a), (ii) 1 to 90%, preferably 5 to 80%, and more preferably 10 to 70% of recurring units of formula (2-2) based on the monomer of formula (2a), (iii) 0 to 50%, preferably 0 to 40%, and more preferably 0 to 30% of recurring units of formula (M5-2) to (M8-2) based on the monomers of formula (M5a) to (M8a), and (iv) 0 to 50%, preferably 0 to 40%, and more preferably 0 to 30% of recurring units based on another monomer.

A variety of copolymerization reaction methods may be used for the preparation of the polymer according to the invention. The preferred polymerization reaction is radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

Resist Composition

Since the polymer of the invention is useful as the base resin of a resist composition, the other aspect of the invention provides a resist composition, especially a chemically amplified positive resist composition, comprising the polymer. Typically, the resist composition contains the polymer, a photoacid generator, and an organic solvent, and other optional components.

Photoacid Generator

The photoacid generator is a compound capable of generating an acid upon exposure to high energy radiation or electron beams and includes the following:

(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives, and
(ix) sulfonate derivatives.

These photoacid generators are described in detail.
(i) Onium salts of formula (P1a-1), (P1a-2) or (P1b):

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

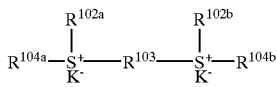

P1b

Herein, $R^{102a}$ and $R^{102b}$ independently represent straight, branched or cyclic alkyl groups of 1 to 8 carbon atoms. $R^{103}$ represents a straight, branched or cyclic alkylene groups of 1 to 10 carbon atoms. $R^{104a}$ and $R^{104b}$ independently represent 2-oxoalkyl groups of 3 to 7 carbon atoms. $K^{31}$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane derivatives of formula (P2)

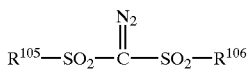

P2

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methyl-phenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime derivatives of formula (P3)

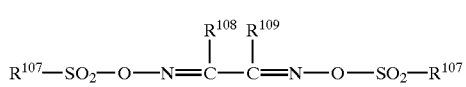

P3

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone derivatives of formula (P4)

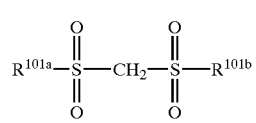

P4

Herein, $R^{101a}$ and $R^{101b}$ are as defined above.

(v) Sulfonic acid esters of N-hydroxyimide compounds of formula (P5)

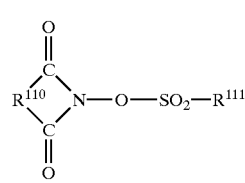

P5

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, 1,2-ethylene, 1,3-propylene, 1,4-butylene, 1-phenyl-1,2-ethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the photoacid generator include:

onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylenebis[methyl(2-oxocyclopentyl)sulfonium trifluoromethanesulfonate], and 1,2'-naphthylcarbonylmethyltetrahydrothiophenium triflate;

diazomethane derivatives such as bis(benzene-sulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutyl-sulfonyl)diazomethane, bis(sec-butylsulfonyl)diazomethane, bis(n-propylsulfonyl)diazomethane, bis(isopropyl-sulfonyl)diazomethane, bis(tert-butylsulfonyl)diazomethane, bis(n-amylsulfonyl)diazomethane, bis(isoamyl-sulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-O-(p-toluene-sulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butane-sulfonyl)-α-dicyclohexylglyoxime, bis-O-(n-butanesulfonyl)-2,3-pentanedioneglyoxime, bis-O-(n-butanesulfonyl)-2-methyl-3,4-pentanedioneglyoxime, bis-O-(methanesulfonyl)-α-dimethylglyoxime, bis-O-(trifluoromethanesulfonyl)-α-dimethylglyoxime, bis-O-(1,1,1-trifluoroethanesulfonyl)-α-dimethylglyoxime, bis-O-(tert-butanesulfonyl)-α-dimethyl-glyoxime, bis-O-(perfluorooctanesulfonyl)-α-dimethylglyoxime, bis-O-(cyclohexanesulfonyl)-α-dimethylglyoxime, bis-O-(benzenesulfonyl)-α-dimethylglyoxime, bis-O-(p-fluoro-benzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfone derivatives such as 2-cyclohexylcarbonyl-2-(p-toluenesulfonyl)propane and 2-isopropylcarbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris-(methanesulfonyloxy)benzene, 1,2,3-tris(trifluoromethanesulfonyloxy)benzene, and 1,2,3-tris(p-toluenesulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzene-sulfonate, N-hydroxyphthalimide trifluoromethanesulfonate, N-hydroxyphthalimide p-toluenesulfonate, N-hydroxynaphthalimide methanesulfonate, N-hydroxynaphthalimide benzene-sulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl) sulfonium trifluoromethanesulfonate, triphenylsulfonium p-toluenesulfonate, (p-tert-butoxyphenyl) diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocylohexyl)sulfonium trifluoromethanesulfonate, and 1,2'-naphthylcarbonylmethyltetrahydrothiophenium triflate; diazomethane derivatives such as bis(benzenesulfonyl) diazomethane, bis(p-toluene-sulfonyl)diazomethane, bis (cyclohexylsulfonyl)diazomethane, bis(n-butylsulfonyl) diazomethane, bis(isobutyl-sulfonyl)diazomethane, bis(sec-butylsulfonyl)diazomethane, bis(n-propylsulfonyl) diazomethane, bis(isopropyl-sulfonyl)diazomethane, and bis(tert-butylsulfonyl)diazo-methane; glyoxime derivatives such as bis-O-(p-toluene-sulfonyl)-α-dimethylglyoxime and bis-O-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxy-naphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 15 parts, and especially 0.5 to 8 parts by weight, per 100 parts by weight of the base resin (all parts are by weight, hereinafter). Less than 0.1 part of the photoacid generator would provide a poor sensitivity whereas more than 15 parts of the photoacid generator would adversely affect transparency and resolution.

Organic Solvent

The organic solvent used herein may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in combinations of two or more thereof. Of the above organic solvents, it is recommended to use diethylene glycol dimethyl ether and 1-ethoxy-2-propanol because the photoacid generator is most soluble therein, propylene glycol monomethyl ether acetate because it is a safe solvent, or a mixture thereof.

An appropriate amount of the organic solvent used is about 200 to 1,000 parts, especially about 400 to 800 parts by weight per 100 parts by weight of the base resin.

Other Polymer

To the resist composition of the invention, another polymer other than the inventive polymer comprising recurring units of formula (1-1) or (1-2) may also be added. The other polymers that can be added to the resist composition are, for example, those polymers comprising units of the following formula (R1) and/or (R2) and having a weight average molecular weight of about 1,000 to about 500,000, especially about 5,000 to about 100,000 although the other polymers are not limited thereto.

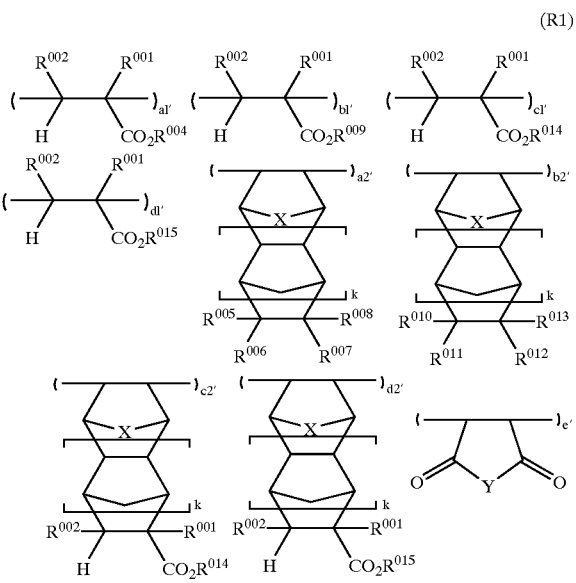

(R1)

-continued

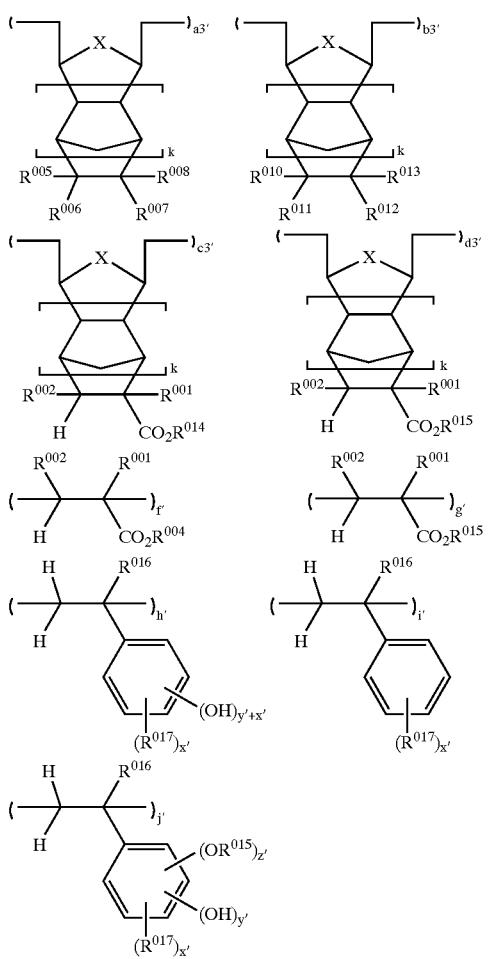
(R2)

Herein, $R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms. $R^{004}$ is hydrogen or a monovalent hydrocarbon group of 1 to 15 carbon atoms having a carboxyl or hydroxyl group. At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. $R^{009}$ is a monovalent hydrocarbon group of 3 to 15 carbon atoms containing a —$CO_2$— partial structure. At least one of $R^{010}$ to $R^{013}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. $R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently single bonds or straight, branched or cyclic alkylene groups of 1 to 15 carbon atoms. $R^{014}$ is a polycyclic hydrocarbon group having 7 to 15 carbon atoms or an alkyl group containing a polycyclic hydrocarbon group. $R^{015}$ is an acid labile group. $R^{016}$ is hydrogen or methyl. $R^{017}$ is a straight, branched or cyclic alkyl group of 1 to 8 carbon atoms. X is $CH_2$ or an oxygen atom. Y is an oxygen atom or $NR^{018}$ wherein $R^{018}$ is a straight, branched or cyclic alkyl group of 1 to 6 carbon atoms. Letter k is equal to 0 or 1; a1', a2', a3', b1', b2', b3', c1', c2', c3', d1', d2', d3', and e' are numbers from 0 to less than 1, satisfying a1'+a2'+a3'+b1'+b2'+b3'+c1'+c2'+c3'+d1'+d2'+d3'+e'=1; f', g', h', i', and j' are numbers from 0 to less than 1, satisfying f'+g'+h'+i'+j'=1.

Exemplary groups of these R's are as exemplified above.

The inventive polymer (comprising recurring units of formula (1-1) or (1-2)) and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The other polymer is not limited to one type and a mixture of two or more other polymers may be added. The use of plural polymers allows for easy adjustment of resist properties.

Dissolution Regulator

To the resist composition, a dissolution regulator may be added. The dissolution regulator is a compound having on the molecule at least two phenolic hydroxyl groups, in which an average of from 0 to 100 mol % of all the hydrogen atoms on the phenolic hydroxyl groups are replaced with acid labile groups or a compound having on the molecule at least one carboxyl group, in which an average of 50 to 100 mol % of all the hydrogen atoms on the carboxyl groups are replaced with acid labile groups, both the compounds having an average molecular weight within a range of 100 to 1,000, and preferably 150 to 800.

The degree of substitution of the hydrogen atoms on the phenolic hydroxyl groups with acid labile groups is on average at least 0 mol %, and preferably at least 30 mol %, of all the phenolic hydroxyl groups. The upper limit is 100 mol %, and preferably 80 mol %. The degree of substitution of the hydrogen atoms on the carboxyl groups with acid labile groups is on average at least 50 mol %, and preferably at least 70 mol %, of all the carboxyl groups, with the upper limit being 100 mol %.

Preferable examples of such compounds having two or more phenolic hydroxyl groups or compounds having at least one carboxyl group include those of formulas (D1) to (D14) below.

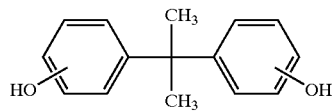
D1

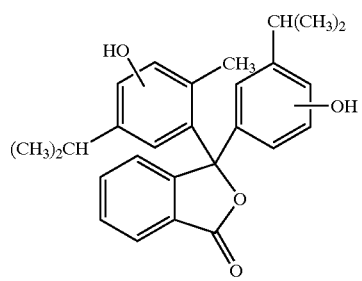
D2

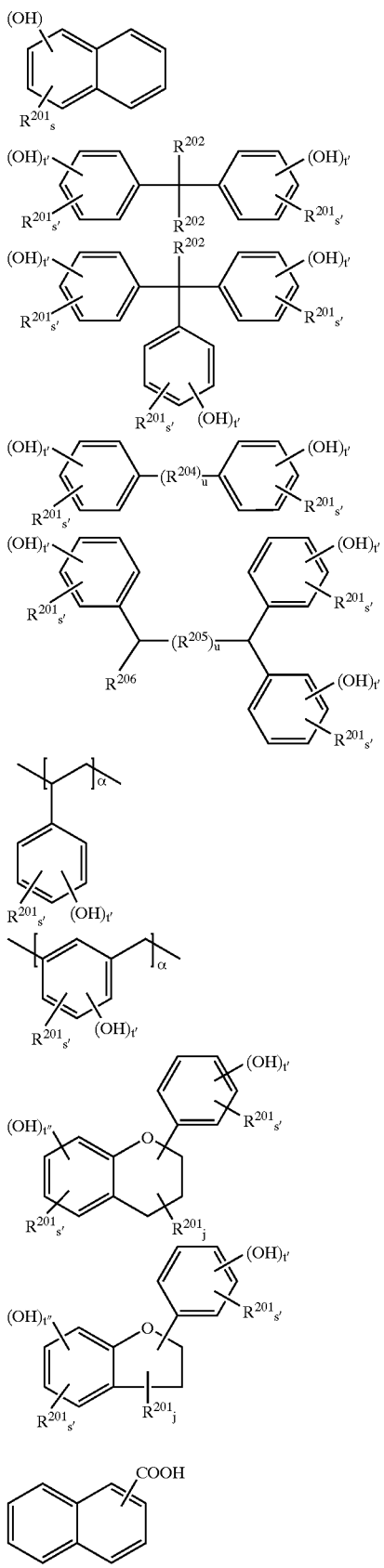
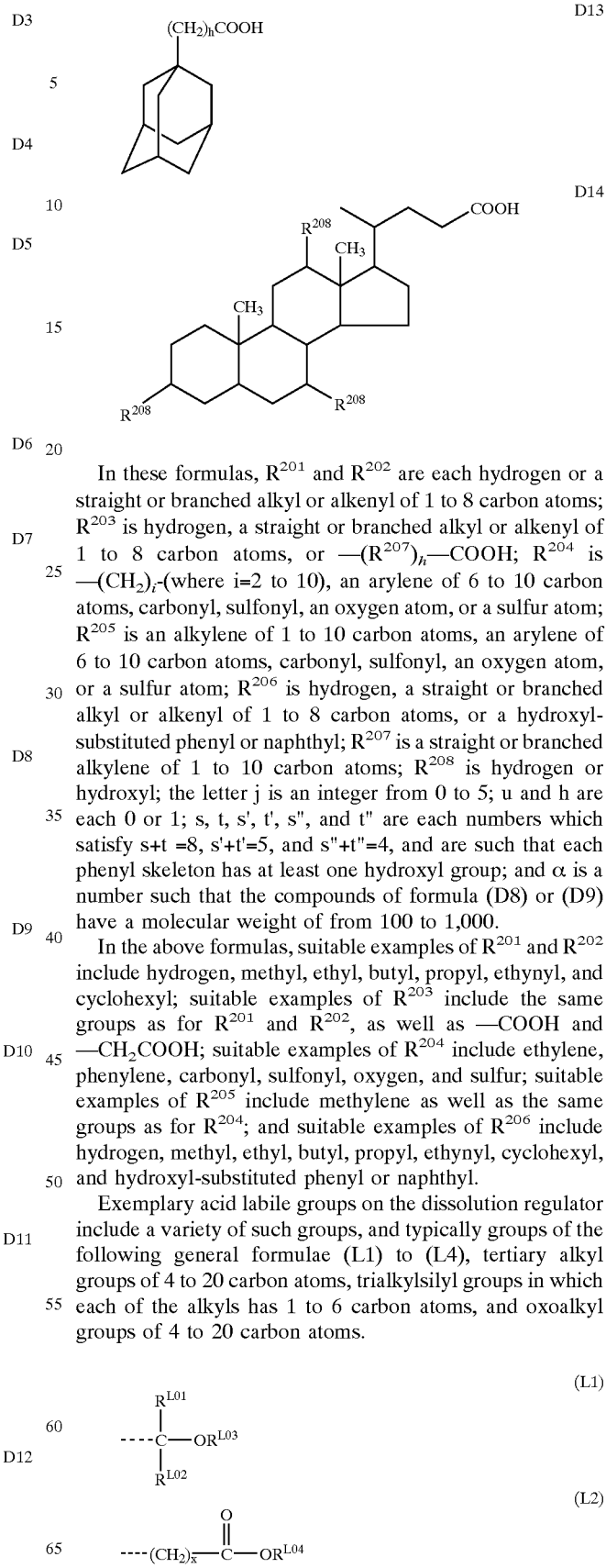

In these formulas, $R^{201}$ and $R^{202}$ are each hydrogen or a straight or branched alkyl or alkenyl of 1 to 8 carbon atoms; $R^{203}$ is hydrogen, a straight or branched alkyl or alkenyl of 1 to 8 carbon atoms, or $-(R^{207})_h-COOH$; $R^{204}$ is $-(CH_2)_i-$ (where i=2 to 10), an arylene of 6 to 10 carbon atoms, carbonyl, sulfonyl, an oxygen atom, or a sulfur atom; $R^{205}$ is an alkylene of 1 to 10 carbon atoms, an arylene of 6 to 10 carbon atoms, carbonyl, sulfonyl, an oxygen atom, or a sulfur atom; $R^{206}$ is hydrogen, a straight or branched alkyl or alkenyl of 1 to 8 carbon atoms, or a hydroxyl-substituted phenyl or naphthyl; $R^{207}$ is a straight or branched alkylene of 1 to 10 carbon atoms; $R^{208}$ is hydrogen or hydroxyl; the letter j is an integer from 0 to 5; u and h are each 0 or 1; s, t, s', t', s", and t" are each numbers which satisfy s+t =8, s'+t'=5, and s"+t"=4, and are such that each phenyl skeleton has at least one hydroxyl group; and α is a number such that the compounds of formula (D8) or (D9) have a molecular weight of from 100 to 1,000.

In the above formulas, suitable examples of $R^{201}$ and $R^{202}$ include hydrogen, methyl, ethyl, butyl, propyl, ethynyl, and cyclohexyl; suitable examples of $R^{203}$ include the same groups as for $R^{201}$ and $R^{202}$, as well as $-COOH$ and $-CH_2COOH$; suitable examples of $R^{204}$ include ethylene, phenylene, carbonyl, sulfonyl, oxygen, and sulfur; suitable examples of $R^{205}$ include methylene as well as the same groups as for $R^{204}$; and suitable examples of $R^{206}$ include hydrogen, methyl, ethyl, butyl, propyl, ethynyl, cyclohexyl, and hydroxyl-substituted phenyl or naphthyl.

Exemplary acid labile groups on the dissolution regulator include a variety of such groups, and typically groups of the following general formulae (L1) to (L4), tertiary alkyl groups of 4 to 20 carbon atoms, trialkylsilyl groups in which each of the alkyls has 1 to 6 carbon atoms, and oxoalkyl groups of 4 to 20 carbon atoms.

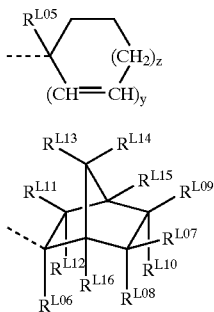

In these formulas, $R^{L01}$ and $R^{L02}$ are each hydrogen or a straight, branched or cyclic alkyl having 1 to 18 carbon atoms; and $R^{L03}$ is a monovalent hydrocarbon group of 1 to 18 carbon atoms which may contain a heteroatom (e.g., oxygen). A pair of $R^{L01}$ and $R^{L02}$, a pair of $R^{L01}$ and $R^{L03}$ or a pair of $R^{L02}$ and $R^{L03}$ may together form a ring, with the proviso that $R^{L01}$, $R^{L02}$, and $R^{L03}$ are each a straight or branched alkylene of 1 to 18 carbon atoms when they form a ring. $R^{L04}$ is a tertiary alkyl group of 4 to 20 carbon atoms, a trialkysilyl group in which each of the alkyls has 1 to 6 carbon atoms, an oxoalkyl group of 4 to 20 carbon atoms, or a group of the formula (L1). $R^{L05}$ is a monovalent hydrocarbon groups of 1 to 8 carbon atoms which may contain a hetero atom or a substituted or unsubstituted aryl group of 6 to 20 carbon atoms. $R^{L06}$ is a monovalent hydrocarbon groups of 1 to 8 carbon atoms which may contain a hetero atom or a substituted or unsubstituted aryl group of 6 to 20 carbon atoms. $R^{L07}$ to $R^{L06}$ independently represent hydrogen or monovalent hydrocarbon groups of 1 to 15 carbon atoms which may contain a hetero atom. Alternatively, $R^{L07}$ to $R^{L16}$, taken together, may form a ring. Each of $R^{L07}$ to $R^{L16}$ represents a divalent $C_1$–$C_{15}$ hydrocarbon group which may contain a hetero atom, when they form a ring. Two of $R^{L07}$ to $R^{L16}$ which are attached to adjoining carbon atoms may bond together directly to form a double bond. Letter x is an integer of 0 to 6. Letter y is equal to 0 or 1, z is equal to 0, 1, 2 or 3, and 2y+z is equal to 2 or 3. Illustrative examples of these groups are as previously exemplified.

The dissolution regulator may be formulated in an amount of 0 to 50 parts, preferably 0 to 40 parts, and more preferably 0 to 30 parts, per 100 parts of the base resin, and may be used singly or as a mixture of two or more thereof. The use of more than 50 parts would lead to slimming of the patterned film, and thus a decline in resolution.

The dissolution regulator can be synthesized by introducing acid labile groups into a compound having phenolic hydroxyl or carboxyl groups in accordance with an organic chemical formulation.

Basic Compound

In the resist composition of the invention, a basic compound may be blended. A suitable basic compound used herein is a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylene-diamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-amino-ethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (B1) may also be included alone or in admixture.

$$N(X)_n(Y)_{3-n} \quad (B1)$$

In the formula, n is equal to 1, 2 or 3; side chain Y is independently hydrogen or a straight, branched or cyclic alkyl group of 1 to 20 carbon atoms which may contain a hydroxyl group or ether; and side chain X is independently selected from groups of the following general formulas (X1) to (X3), and two or three X's may bond together to form a ring.

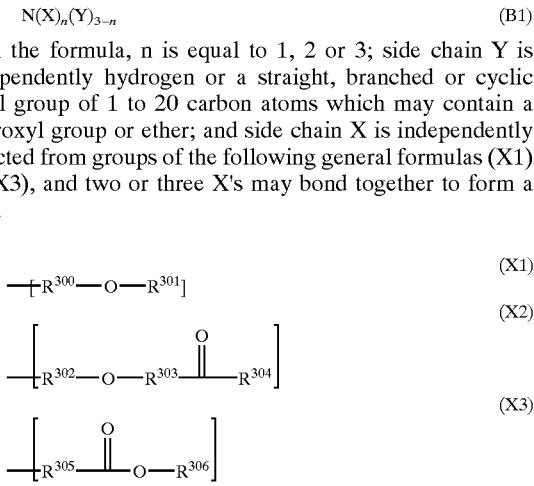

In the formulas, $R^{300}$, $R^{302}$ and $R^{305}$ are independently straight or branched alkylene groups of 1 to 4 carbon atoms; $R^{301}$ and $R^{304}$ are independently hydrogen, straight, branched or cyclic alkyl groups of 1 to 20 carbon atoms, which may contain at least one hydroxyl group, ether, ester or lactone ring; $R^{303}$ is a single bond or a straight or branched alkylene group of 1 to 4 carbon atoms; and $R^{306}$ is a single bond or a straight, branched or cyclic alkyl group of 1 to 20 carbon atoms which may contain one or more hydroxyl groups, ether groups, ester groups or lactone rings.

Illustrative examples of the compounds of formula (B1) include tris(2-methoxymethoxyethyl)amine, tris{2-(methoxyethoxy)ethyl}amine, tris{2-(2-methoxyethoxymethoxy)ethyl}-amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonyl-ethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-((2-methoxyethyl))-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

The basic compound is preferably formulated in an amount of 0.001 to 10 parts, and especially 0.01 to 1 part, per part of the photoacid generator. Less than 0.001 part of the basic compound may fail to achieve the desired effects thereof, while the use of more than 10 parts would result in too low a sensitivity and resolution.

Other Components

In the resist composition, a compound bearing a ≡C—COOH group in a molecule may be blended. Exemplary, non-limiting compounds bearing a ≡C—COOH group include one or more compounds selected from Groups I and II below. Including this compound improves the PED stability of the resist and ameliorates edge roughness on nitride film substrates.

Group I:

Compounds in which some or all of the hydrogen atoms on the phenolic hydroxyl groups of the compounds of general formulas (A1) to (A10) below have been replaced with —$R^{401}$—COOH (wherein $R^{401}$ is a straight or branched alkylene of 1 to 10 carbon atoms), and in which the molar ratio C/(C+D) of phenolic hydroxyl groups (C) to ≡C—COOH groups (D) in the molecule is from 0.1 to 1.0.

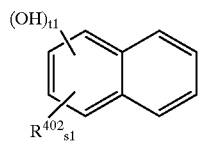

A1

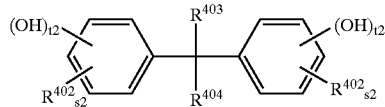

A2

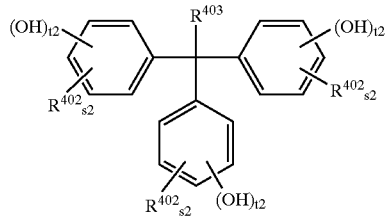

A3

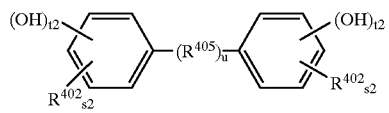

A4

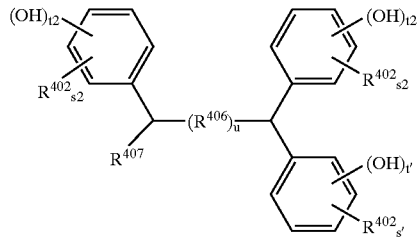

A5

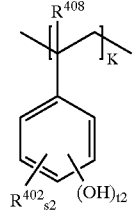

A6

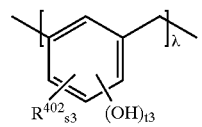

A7

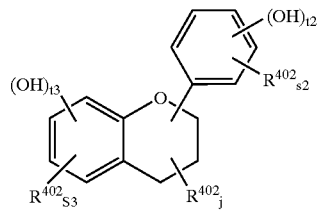

A8

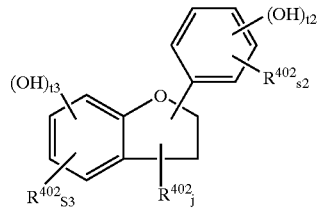

A9

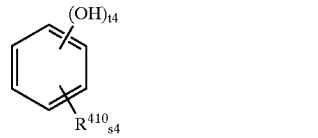

A10

In these formulas, $R^{408}$ is hydrogen or methyl; $R^{402}$ and $R^{403}$ are each hydrogen or a straight or branched alkyl or alkenyl of 1 to 8 carbon atoms; $R^{404}$ is hydrogen, a straight or branched alkyl or alkenyl of 1 to 8 carbon atoms, or a —$(R^{409})_h$—COOR' group (R' being hydrogen or —$R^{409}$—COOH); $R^{405}$ is —$(CH_2)_i$— (wherein i is 2 to 10), an arylene of 6 to 10 carbon atoms, carbonyl, sulfonyl, an oxygen atom, or a sulfur atom; $R^{406}$ is an alkylene of 1 to 10 carbon atoms, an arylene of 6 to 10 carbon atoms, carbonyl, sulfonyl, an oxygen atom, or a sulfur atom; $R^{407}$ is hydrogen, a straight or branched alkyl or alkenyl of 1 to 8 carbon atoms, or a hydroxyl-substituted phenyl or naphthyl; $R^{409}$ is a straight or branched alkylene of 1 to 10 carbon atoms; $R^{410}$ is hydrogen, a straight or branched alkyl or alkenyl of 1 to 8 carbon atoms, or a —$R^{411}$—COOH group; $R^{411}$ is a straight or branched alkylene of 1 to 10 carbon atoms; the letter j is an integer from 0 to 5; u and h are each 0 or 1; s1, t1, s2, t2, s3, t3, s4, and t4 are each numbers which satisfy s1+t1=8, s2+t2=5, s3+t3=4, and s4+t4=6, and are such that each phenyl skeleton has at least one hydroxyl group; κ is a number such that the compound of formula (A6) may have a weight average molecular weight of 1,000 to 5,000; and λ is a number such that the compound of formula (A7) may have a weight average molecular weight of 1,000 to 10,000.

Group II:

Compounds of general formulas (A11) to (A15) below.

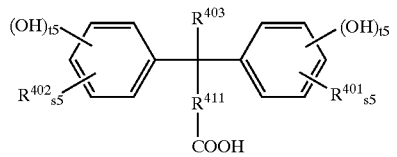
A11

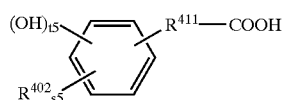
A12

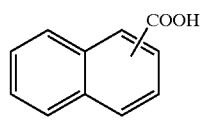
A13

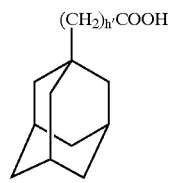
A14

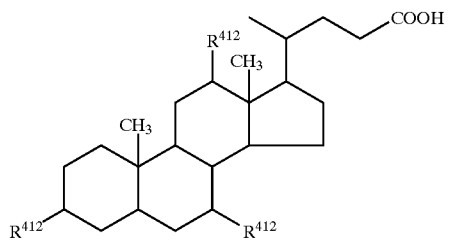
A15

In these formulas, $R^{402}$, $R^{403}$, and $R^{411}$ are as defined above; $R^{412}$ is hydrogen or hydroxyl; s5 and t5 are numbers which satisfy $s5 \geq 0$, $t5 \geq 0$, and $s5+t5=5$; and h' is equal to 0 or 1.

Illustrative, non-limiting examples of the compound bearing a $\equiv$C—COOH group include compounds of the general formulas AI-1 to AI-14 and AII-1 to AII-10 below.

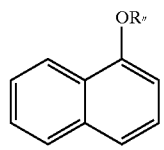
AI-1

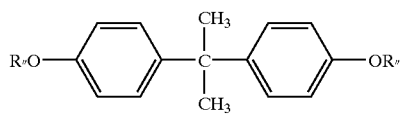
AI-2

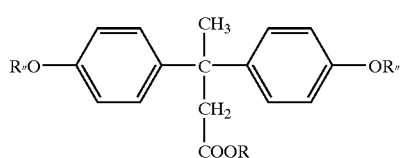
AI-3

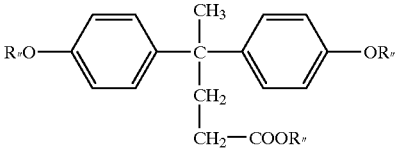
AI-4

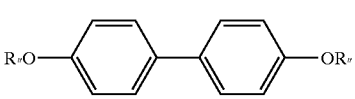
AI-5

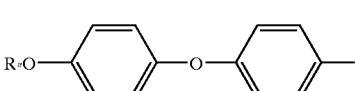
AI-6

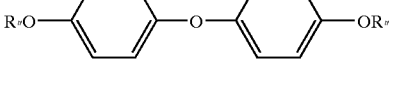
AI-7

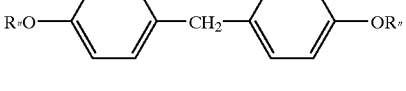
AI-8

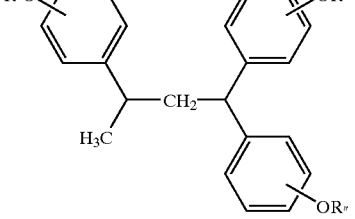
AI-9

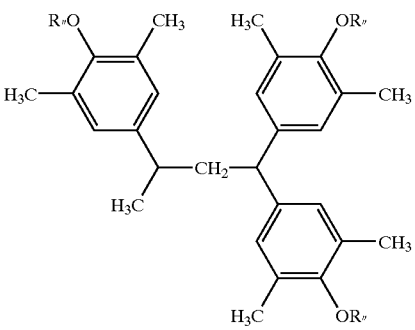
AI-10

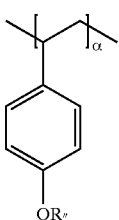

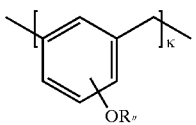
AI-11

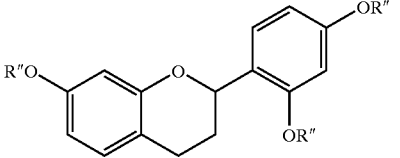
AI-12

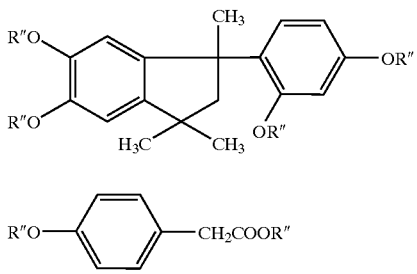

AI-13

AI-14

In the above formulas, R" is hydrogen or a CH$_2$COOH group such that the CH$_2$COOH group accounts for 10 to 100 mol % of R" in each compound, α and κ are as defined above.

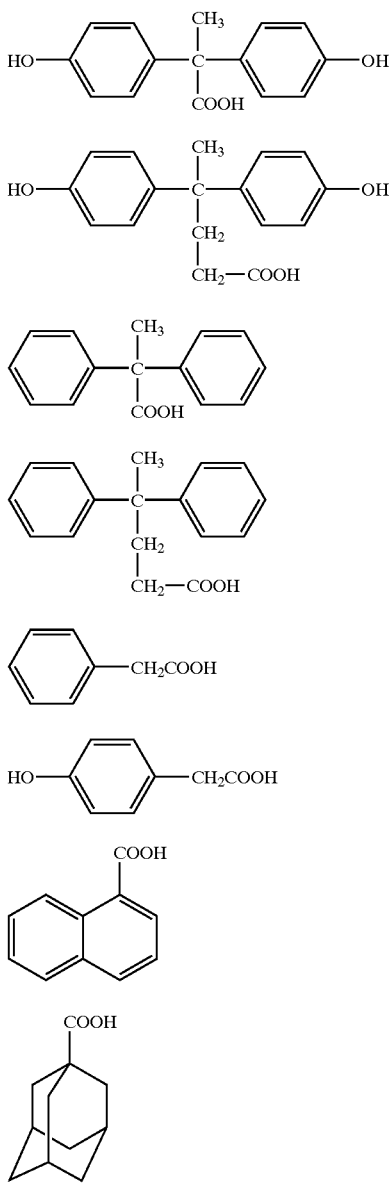

AII-1

AII-2

AII-3

AII-4

AII-5

AII-6

AII-7

AII-8

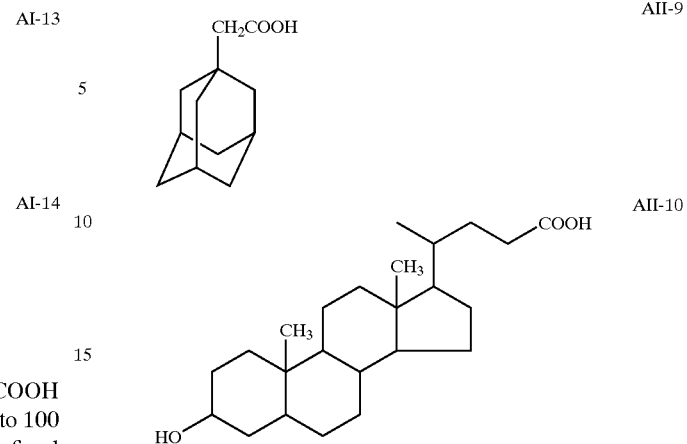

AII-9

AII-10

The compound bearing a ≡C—COOH group within the molecule may be used singly or as combinations of two or more thereof.

The compound bearing a ≡C—COOH group within the molecule is added in an amount ranging from 0 to 5 parts, preferably 0.1 to 5 parts, more preferably 0.1 to 3 parts, further preferably 0.1 to 2 parts, per 100 parts of the base resin. More than 5 parts of the compound can reduce the resolution of the resist composition.

The resist composition of the invention may additionally include an acetylene alcohol derivative for the purpose of enhancing the shelf stability. Preferred acetylene alcohol derivatives are those having the general formula (S1) or (S2) below.

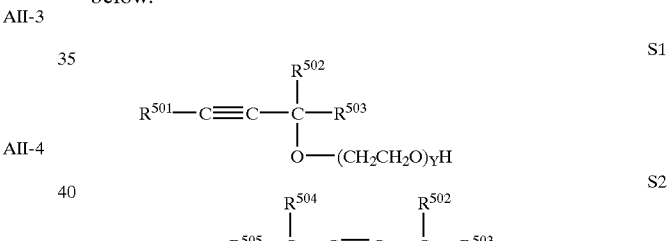

S1

S2

In the formulas, $R^{501}$, $R^{502}$, $R^{503}$, $R^{504}$, and $R^{505}$ are each hydrogen or a straight, branched, or cyclic alkyl of 1 to 8 carbon atoms; and X and Y are each 0 or a positive number, satisfying $0 \leq X \leq 30$, $0 \leq Y \leq 30$, and $0 \leq X+Y \leq 40$.

Preferable examples of the acetylene alcohol derivative include Surfynol 61, Surfynol 82, Surfynol 104, Surfynol 104E, Surfynol 104H, Surfynol 104A, Surfynol TG, Surfynol PC, Surfynol 440, Surfynol 465, and Surfynol 485 from Air Products and Chemicals Inc., and Surfynol E1004 from Nisshin Chemical Industry K.K.

The acetylene alcohol derivative is preferably added in an amount of 0.01 to 2% by weight, and more preferably 0.02 to 1% by weight, per 100% by weight of the resist composition. Less than 0.01% by weight would be ineffective for improving coating characteristics and shelf stability, whereas more than 2% by weight would result in a resist having a low resolution.

The resist composition of the invention may include optional ingredients, for example, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Florade FC-430 and FC-431 from Sumitomo 3M, Ltd., Surflon S-141 and S-145 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Florade FC-430 from Sumitomo 3M, Ltd. and X-70-093 from Shin-Etsu Chemical Co., Ltd.

Pattern formation using the resist composition of the invention may be carried out by a known lithographic technique. For example, the resist composition is applied onto a substrate such as a silicon wafer by spin coating or the like to form a resist film having a thickness of 0.2 to 2.0 μm, which is then pre-baked on a hot plate at 60 to 150° C. for 1 to 10 minutes, and preferably at 80 to 130° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm$^2$, and preferably about 5 to 100 mJ/cm$^2$, then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 248 to 193 nm, an excimer laser, x-rays, or an electron beam. The desired pattern may not be obtainable outside the upper and lower limits of the above range.

The resist composition comprising the polymer as a base resin lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser, a finely defined pattern having sidewalls perpendicular to the substrate can easily be formed.

EXAMPLE

Synthesis Examples and Examples are given below by way of illustration and not by way of limitation. The abbreviation Mw is a weight average molecular weight, Mn is a number average molecular weight, SEM is scanning electron microscope, and TMAH is tetramethylammonium hydroxide.

Ether compounds and polymers thereof within the scope of the invention were synthesized by the following procedure.

Synthesis Example 1-1
Synthesis of 5-(1-hydroxy-5-methoxypentyl)-2-norbornene (Monomer 1)

In 300 g of tetrahydrofuran was dissolved 122.6 g of 1-chloro-4-methoxybutane. The solution was added dropwise to 24.3 g of metallic magnesium over 2 hours and below 60° C. Agitation was continued for 2 hours at room temperature. To the solution, 122.2 g of 5-norbornene-2-carbaldehyde was added dropwise over one hour and below 50° C. Agitation was continued for one hour at room temperature to drive the reaction to completion. Then 300 g of water and 44 g of 20% HCl were added to the solution, which was agitated. Extraction with 500 g of hexane gave the organic layer, which was washed with water, dried over anhydrous sodium sulfate, filtered, and concentrated in vacuum. The oily matter thus obtained was distilled in vacuum, obtaining 158.6 g of 5-(1-hydroxy-5-methoxypentyl)-2-norbornene. The yield was 75.4%.

IR (thin film): ν=3415 (br.), 3057, 2937, 2866, 1458, 1450, 1389, 1120, 719 cm$^{-1}$ $^1$H-NMR (300 MHz in CDCl$_3$) of 5-(1-hydroxy-5-methoxypentyl)-2-norbornene (exo form:endo form=45:55): δ=0.46–0.52 (0.55H, ddd, J=11.6, 4.7, 2.5 Hz), 0.88–0.94 (0.45H, ddd, J=11.6, 4.1, 2.5 Hz), 1.19–1.67 (9H, m), 1.70–1.78 (0.55H, ddd, J=11.6, 9.4, 3.9 Hz), 1.81–1.89 (0.45H, ddd, J=11.6, 8.8, 3.9 Hz), 1.96–2.09 (1H, m), 2.76–3.04 (3H, m), 3.30–3.41 (5H, m) (inclusive of 3.30 (1.65H, s), 3.31 (1.35H, s)), 5.85–5.88 (0.45H, m), 5.97–6.00 (0.55H, m), 6.01–6.15 (1H, m)

Synthesis Example 1-2
Synthesis of 5-(1-acetoxy-5-methoxypentyl)-2-norbornene (Monomer 2)

In 63.3 g of pyridine, 105.2 g of 5-(1-hydroxy-5-methoxypentyl)-2-norbornene (Monomer 1) was reacted with 61.3 g of acetic anhydride in the presence of 2 g of 4-dimethylaminopyridine at room temperature for 10 hours. The reaction was stopped by adding 30 g of water. Extraction with hexane gave the organic layer, which was washed with water, dried over anhydrous sodium sulfate, filtered, and concentrated in vacuum. The oily matter thus obtained was distilled in vacuum, obtaining 122.4 g of 5-(1-acetoxy-5-methoxypentyl)-2-norbornene. The yield was 97.0%.

IR (thin film): ν=3057, 2939, 2868, 1734, 1458, 1373, 1338, 1244, 1120, 1020, 723 cm$^{-1}$ $^1$H-NMR (270 MHz in CDCl$_3$) of 5-(1-acetoxy-5-methoxypentyl)-2-norbornene (exo form:endo form=45:55): δ=0.52–0.59 (0.55H, ddd, J=11.7, 4.9, 2.4 Hz), 0.70–0.77 (0.45H, ddd, J=11.7, 4.4, 2.4 Hz), 1.10–1.82 (10H, m), 1.98 (1.35H, s), 2.05 (1.65H, s), 2.15–2.57 (1H, m), 2.76 (2H, br. s), 3.29 (1.65H, s), 3.30 (1.35H, s), 4.29–4.46 (1H, m), 5.85–5.90 (1H, m), 6.11–6.18 (1H, m)

Synthesis Example 1-3
Synthesis of 5-{2-(2-hydroxy-6-methoxyhexyl)1}-2-norbornene (Monomer 3)

The procedure of Synthesis Example 1-1 was repeated except that 5-acetyl-2-norbornene was used instead of 5-norbornene-2-carbaldehyde. In this way, 5-{2-(2-hydroxy-6-methoxyhexyl)}-2-norbornene was synthesized in a yield of 74%.

IR (thin film): ν=3572, 3485 (br.), 3057, 2968, 2939, 2868, 1710, 1682, 1570, 1464, 1460, 1373, 1369, 1338, 1294, 1271, 1255, 1238, 1196, 1119, 931, 742, 719 cm$^{-1}$ $^1$H-NMR (300 MHz in CDCl$_3$) of 5-{2-(2-hydroxy-6-methoxyhexyl)}-2-norbornene (exo form:endo form=48:52): δ=1.00 (1.44H, s), 1.05–1.16 (2.56H, m) (inclusive of 1.16 (1.56H, s)), 1.18–1.63 (9H, m), 1.74–1.86 (1H, m), 2.18–2.25 (1H, m), 2.80 (1H, br. s), 2.91 (1H, br. s), 3.31–3.41 (5H, m) (inclusive of 3.31 (1.56H, s), 3.32 (1.44H, s)), 6.06–6.10 (1H, m), 6.20–6.24 (1H, m)

Synthesis Example 1-4

Synthesis of 5-(2-acetoxy-5-methoxypentyl)-2-norbornene (Monomer 4)

The procedure of Synthesis Example 1-1 was repeated except that (5-norbornen-2-yl)acetaldehyde was used instead of 5-norbornene-2-carbaldehyde. In this way, 5-(2-hydroxy-5-methoxypentyl)-2-norbornene was synthesized in a yield of 73%.

The procedure of Synthesis Example 1-2 was repeated except that 5-(2-hydroxy-5-methoxypentyl)-2-norbornene was used instead of 5-(1-hydroxy-5-methoxypentyl)-2-norbornene. In this way, 5-(2-acetoxy-5-methoxypentyl)-2-norbornene was synthesized in a yield of 95%.

IR (thin film): ν=3057, 2958, 2868, 1736, 1448, 1373, 1244, 1120, 1022, 719 cm$^{-1}$ $^1$H-NMR (270 MHz in CDCl$_3$) of the main isomer (endo form) of 5-(2-acetoxy-5-methoxypentyl)-2-norbornene: δ=0.46–0.57 (1H, m), 1.12–1.63 (8H, m), 1.78–1.88 (1H, m), 1.93–2.01 (4H, m) (inclusive of 2.01 (3H, s)), 2.73 (1H, br. s), 2.78 (1H, br. s), 3.28–3.34 (5H, m) (inclusive of 3.30 (3H, s)), 4.89 (1H, m), 5.85–5.94 (1H, m), 6.07–6.11 (1H, m)

Monomer 1

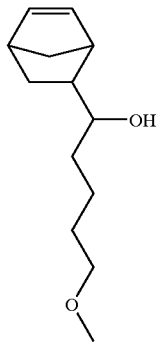

Monomer 2

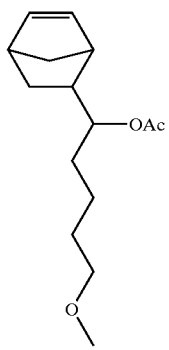

Monomer 3

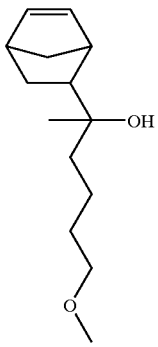

Monomer 4

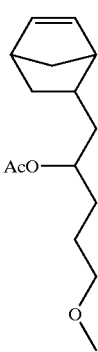

Synthesis Example 2-1

Synthesis of Polymer 1

In 150 ml of tetrahydrofuran were dissolved 42.1 g of Monomer 1, 78.1 g of 2-ethyl-2-norbornyl 5-norbornene-2-carboxylate and 49.0 g of maleic anhydride. To the solution was added 1.8 g of 2,2'-azobis(2-methylbutyronitrile). The solution was stirred for 15 hours at 60° C. and then concentrated in vacuum. The residue was dissolved in 600 ml of tetrahydrofuran, which was added dropwise to 10 liters of n-hexane. The resulting solids were collected by filtration, washed with 10 liters of n-hexane, and vacuum dried for 6 hours at 40° C. There was obtained 86.7 g of a polymer designated Polymer 1 whose structure is shown below. The yield was 51.2%.

A GPC analysis of the polymer showed a Mw of 8,100 on a polystyrene basis and a dispersity Mw/Mn of 1.78. On $^{13}$C-NMR analysis of the polymer, the ratio of Monomer 1/2-ethyl-2-norbornyl 5-norbornene-2-carboxylate/maleic anhydride was 0.2/0.3/0.5.

Synthesis Examples 2-2 to 2-15

Synthesis of Polymers 2 to 15

Polymers 2 to 15 were synthesized by the same procedure as above or a well-known procedure.

(Polymer 1)
(x = 0.20, d = 0.30, e = 0.50,
Mw = 9,800, Mw/Mn = 1.75)
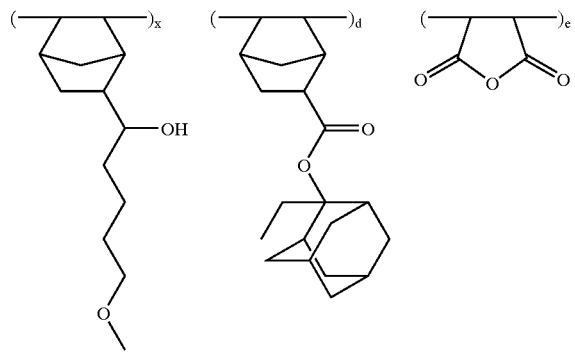
(Polymer 2)
(x = 0.20, d = 0.30, e = 0.50,
Mw = 9,200, Mw/Mn = 1.71)
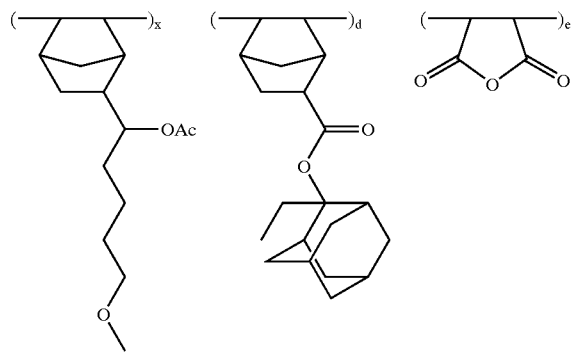
(Polymer 3)
(x = 0.20, d = 0.30, e = 0.50,
Mw = 7,500, Mw/Mn = 1.77)
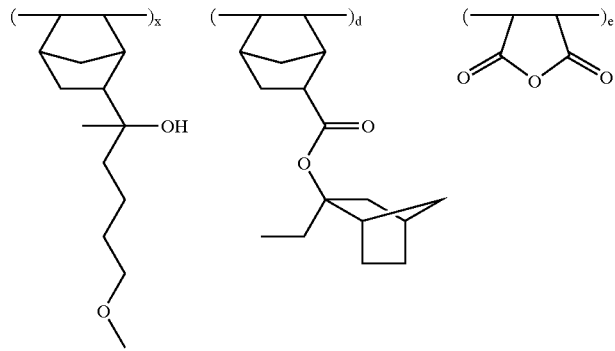
(Polymer 4)
(x = 0.20, d = 0.30, e = 0.50,
Mw = 7,400, Mw/Mn = 1.81)
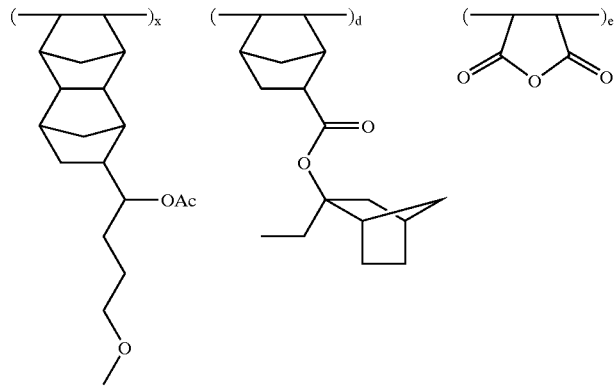

-continued
(Polymer 5)
(x = 0.20, d = 0.30, e = 0.50,
Mw = 7,800, Mw/Mn = 1.85)
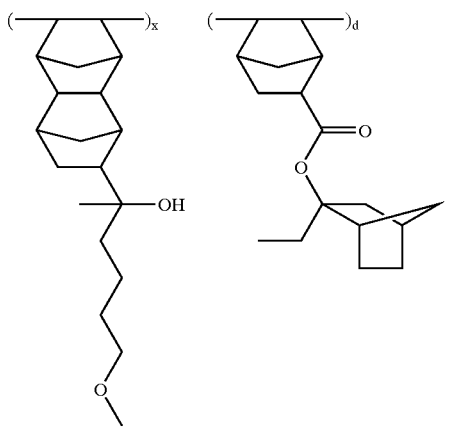
(Polymer 6)
(x = 0.20, d = 0.30, e = 0.50,
Mw = 9,100, Mw/Mn = 1.85)
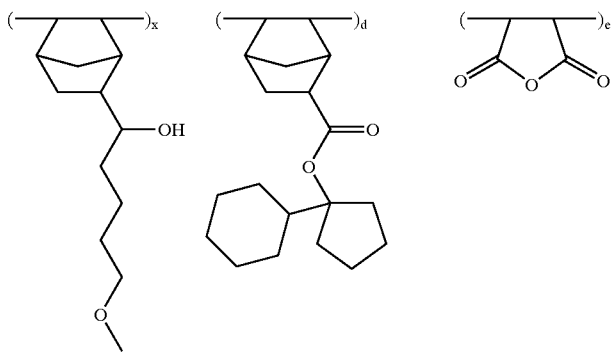
(Polymer 7)
(x = 0.20, d = 0.30, e = 0.50,
Mw = 9,000, Mw/Mn = 1.77)
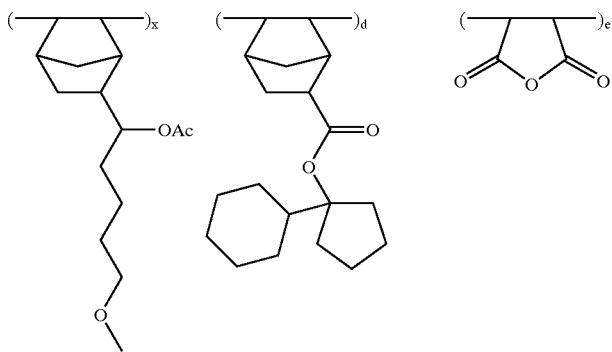
(Polymer 8)
(x = 0.20, d = 0.30, e = 0.50,
Mw = 12,300, Mw/Mn = 1.82)
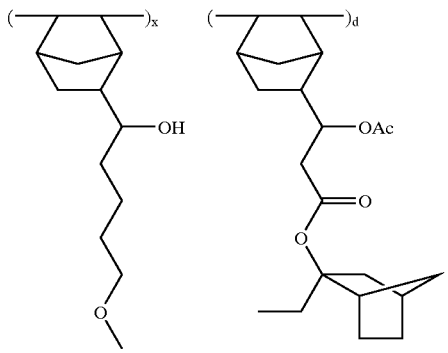

(Polymer 9)
(x = 0.20, d = 0.30, e = 0.50,
Mw = 13,000, Mw/Mn = 1.80)
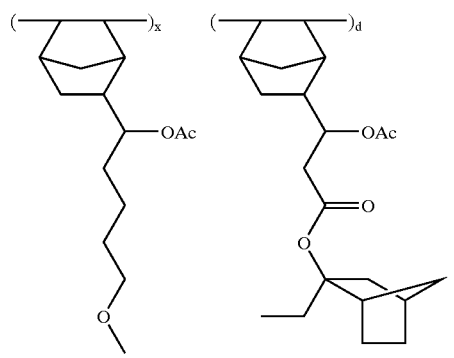
(Polymer 10)
(x = 0.50, d = 0.50,
Mw = 23,100, Mw/Mn = 1.95)
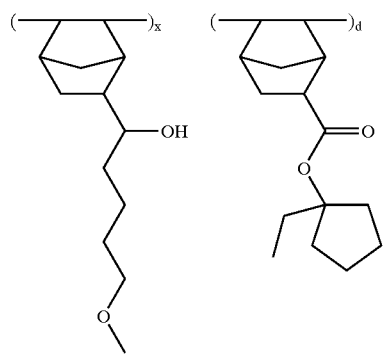
(Polymer 11)
(x = 0.35, d = 0.30, e = 0.35,
Mw = 11,200, Mw/Mn = 1.98)
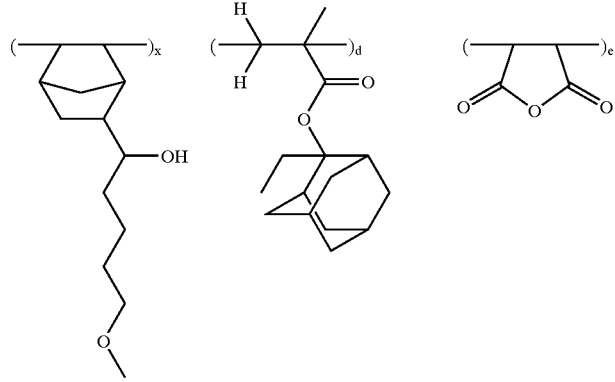
(Polymer 12)
(x = 0.35, d = 0.30, e = 0.35,
Mw = 10,900, Mw/Mn = 2.01)
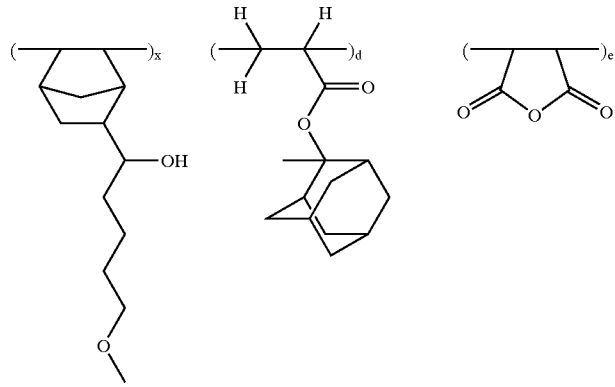

-continued (Polymer 13)
(x = 0.35, d = 0.30, e = 0.35,
Mw = 11,800, Mw/Mn = 2.10)

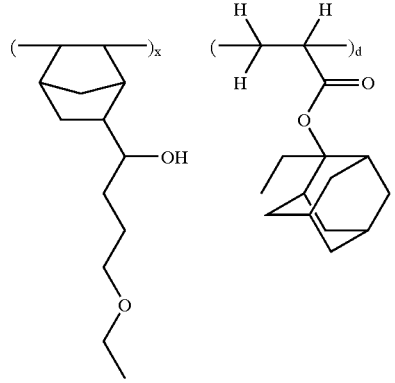

(Polymer 14)
(x = 0.50, d = 0.50,
Mw = 23,900, Mw/Mn = 1.48)

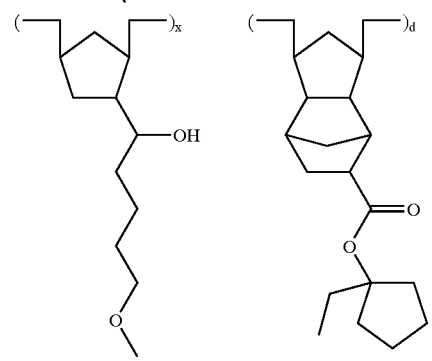

(Polymer 15)
(x = 0.50, d = 0.50,
Mw = 22,600, Mw/Mn = 1.42)

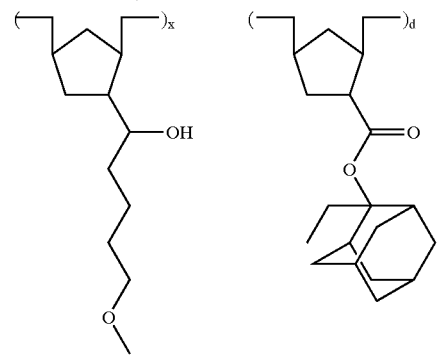

Example I

Resist compositions were formulated using inventive polymers as the base resin and examined for substrate adhesion.

Examples I-1 to I-5 and Comparative Examples 1, 2

Resist compositions were prepared by using inventive polymers (Polymers 1 to 5) or comparative polymers (Polymers 16 and 17 identified below) as the base resin, and dissolving the polymer, a photoacid generator (designated as PAG1), and a basic compound in a solvent in accordance with the formulation shown in Table 1. These compositions were each filtered through a Teflon filter (pore diameter 0.2 μm), thereby giving resist solutions.

(Polymer 16)
(d = 0.50, e = 0.50,
Mw = 8,800, Mw/Mn = 1.80

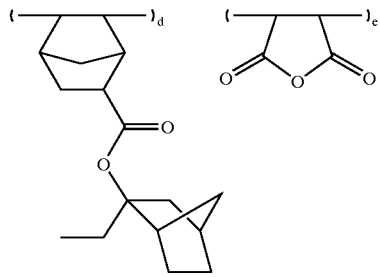

(Polymer 17)
(a = 0.20, d = 0.30, e = 0.50,
Mw = 9,700, Mw/Mn = 1.88

-continued

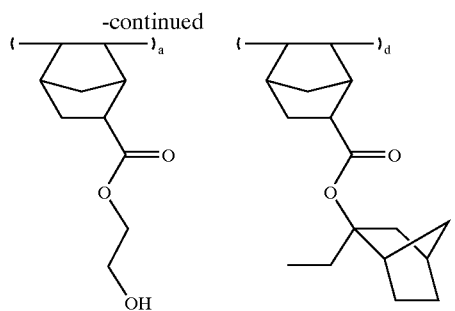

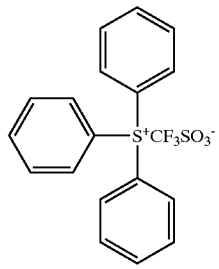

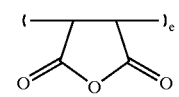

(PAG 1)

These resist solutions were spin coated onto hexamethyldisilazane-spray coated silicon wafers at 90° C. for 40 seconds, then heat treated at 110° C. for 90 seconds to give resist films having a thickness of 0.5 μm. The resist films were exposed using an KrF excimer laser stepper (Nikon Corporation; NA 0.5), then heat treated at 110° C. for 90 seconds, and puddle developed with a solution of 2.38% TMAH in water for 60 seconds, thereby giving 1:1 line-and-space patterns. The wafers as developed were observed under overhead SEM. The minimum width (μm) of lines left unstripped is the limit of adhesion of the resist under test.

The composition and test results of the resist materials are shown in Table 1.

The solvents and basic compound used are propylene glycol methyl ether acetate (PGMEA) and tributyl amine (TBA), respectively. It is noted that the solvent contained 0.01% by weight of surfactant Florade FC-430 (Sumitomo 3M).

TABLE 1

|  |  | Resin (pbw) | Photoacid generator (pbw) | Basic compound (pbw) | Solvent (pbw) | Limit of adhesion, μm |
|---|---|---|---|---|---|---|
| Example | I-1 | Polymer 1 (80) | PAG 1 (1) | TBA (0.078) | PGMEA (480) | 0.24 |
|  | I-2 | Polymer 2 (80) | PAG 1 (1) | TEA (0.078) | PGMEA (480) | 0.23 |
|  | I-3 | Polymer 6 (80) | PAG 1 (1) | TBA (0.078) | PGMEA (480) | 0.24 |
|  | I-4 | Polymer 8 (80) | PAG 1 (1) | TBA (0.078) | PGMEA (480) | 0.22 |
|  | I-5 | Polymer 9 (80) | PAG 1 (1) | TBA (0.078) | PGMEA (480) | 0.23 |
| Comparative Example | 1 | Polymer 16 (80) | PAG 1 (1) | TBA (0.078) | PGMEA (480) | >0.50 |
|  | 2 | Polymer 17 (80) | PAG 1 (1) | TBA (0.078) | PGMEA (480) | >0.50 |

It is evident from Table 1 that the polymers within the scope of the invention have good substrate adhesion.

Example II

Resist compositions were formulated using inventive polymers and examined for resolution upon KrF excimer laser exposure.

Examples II-1 to II-21

Evaluation of Resist Resolution

Resist compositions were prepared by using Polymers 1 to 15 as the base resin, and dissolving the polymer, a photoacid generator (designated as PAG1 and 2), a dissolution regulator (designated as DRR1 to 4), a basic compound, and a compound having a ≡C—COOH group in the molecule (ACC1 and 2) in a solvent in accordance with the formulation shown in Table 2. These compositions were each filtered through a Teflon filter (pore diameter 0.2 μm), thereby giving resist solutions.

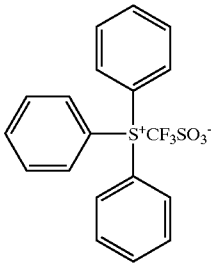

(PAG 1)

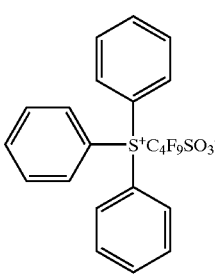

(PAG 2)

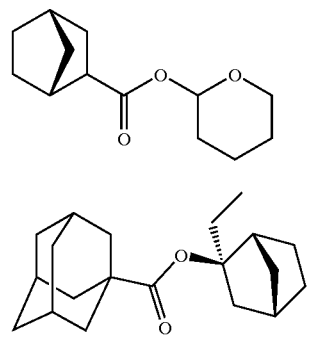
(DRR 1)

(DRR 2)

(DRR 3)

(DRR 4)

(ACC 1)

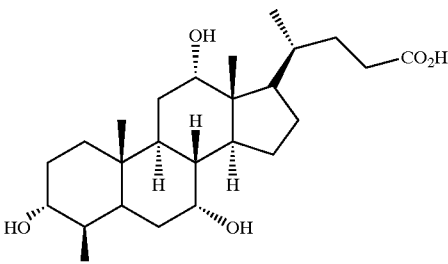
(ACC 2)

The solvent and basic compounds used are as follows. It is noted that the solvent contained 0.01% by weight of surfactant Florade FC-430 (Sumitomo 3M).

PGMEA: propylene glycol methyl ether acetate
TEA: triethanolamine
TMMEA: trismethoxymethoxyethylamine
TMEMEA: trismethoxyethoxymethoxyethylamine These resist solutions were spin coated onto hexamethyldisilazane-spray coated silicon wafers at 90° C. for 90 seconds, then heat treated at 110° C. for 90 seconds to give resist films having a thickness of 0.5 μm. The resist films were exposed using an KrF excimer laser stepper (Nikon Corporation; NA 0.5), then heat treated at 110° C. for 90 seconds, and puddle developed with a solution of 2.38% TMAH in water for 60 seconds, thereby giving 1:1 line-and-space patterns.

The wafers as developed were sectioned and observed under sectional SEM. The optimal dose (Eop, mJ/cm$^2$) was defined as the dose which provided a 1:1 resolution at the top and bottom of a 0.30 μm line-and-space pattern. The resolution of the resist under evaluation was defined as the minimum line width (μm) of the lines and spaces that separated at the optimal dose. The shape of the resolved resist pattern was examined under a SEM.

The composition and test results of the resist materials are shown in Table 2.

TABLE 2

| Example | Resin (pbw) | Photoacid generator (pbw) | Dissolution regulator (pbw) | Basic compound (pbw) | Solvent (pbw) | Eop, mJ/cm$^2$ | Resolution, μm | Shape |
|---|---|---|---|---|---|---|---|---|
| II-1 | Polymer 1 (80) | PAG 1 (1) | | TEA (0.063) | PGMEA (480) | 26.0 | 0.20 | rectangular |
| II-2 | Polymer 2 (80) | PAG 1 (1) | | TEA (0.063) | PGMEA (480) | 25.0 | 0.21 | rectangular |
| II-3 | Polymer 3 (80) | PAG 1 (1) | | TEA (0.063) | PGMEA (480) | 23.0 | 0.22 | rectangular |
| II-4 | Polymer 4 (80) | PAG 1 (1) | | TEA (0.063) | PGMEA (480) | 27.0 | 0.24 | rectangular |
| II-5 | Polymer 5 (80) | PAG 1 (1) | | TEA (0.063) | PGMEA (480) | 28.0 | 0.25 | rectangular |
| II-6 | Polymer 6 (80) | PAG 1 (1) | | TEA (0.063) | PGMEA (480) | 24.0 | 0.20 | rectangular |
| II-7 | Polymer 7 (80) | PAG 1 (1) | | TEA (0.063) | PGMEA (480) | 23.0 | 0.22 | rectangular |
| II-8 | Polymer 8 (80) | PAG 1 (1) | | TEA (0.063) | PGMEA (480) | 22.0 | 0.20 | rectangular |

TABLE 2-continued

| Example | Resin (pbw) | Photoacid generator (pbw) | Dissolution regulator (pbw) | Basic compound (pbw) | Solvent (pbw) | Eop, mJ/cm$^2$ | Resolution, μm | Shape |
|---|---|---|---|---|---|---|---|---|
| II-9 | Polymer 9 (80) | PAG 1 (1) | | TEA (0.063) | PGMEA (480) | 22.0 | 0.21 | rectangular |
| II-10 | Polymer 10 (80) | PAG 1 (1) | | TEA (0.063) | PGMEA (480) | 19.0 | 0.22 | rectangular |
| II-11 | Polymer 11 (80) | PAG 1 (1) | | TEA (0.063) | PGMEA (480) | 21.0 | 0.22 | rectangular |
| II-12 | Polymer 12 (80) | PAG 1 (1) | | TEA (0.063) | PGMEA (560) | 22.0 | 0.23 | rectangular |
| II-13 | Polymer 13 (80) | PAG 1 (1) | | TEA (0.063) | PGMEA (560) | 22.0 | 0.24 | rectangular |
| II-14 | Polymer 14 (80) | PAG 1 (1) | | TEA (0.063) | PGMEA (640) | 21.0 | 0.22 | rectangular |
| II-15 | Polymer 15 (80) | PAG 1 (1) | | TEA (0.063) | PGMEA (640) | 32.0 | 0.21 | rectangular |
| II-16 | Polymer 6 (80) | PAG 2 (1) | | TEA (0.063) | PGMEA (480) | 23.0 | 0.20 | rectangular |
| II-17 | Polymer 6 (80) | PAG 2 (1) | | TMMEA (0.118) | PGMEA (480) | 24.0 | 0.20 | rectangular |
| II-18 | Polymer 6 (80) | PAG 2 (1) | | TMEMEA (0.173) | PGMEA (480) | 26.0 | 0.21 | rectangular |
| II-19 | Polymer 8 (70) | PAG 2 (1) | DRR 1 (10) | TEA (0.063) | PGMEA (480) | 18.0 | 0.21 | rectangular |
| II-20 | Polymer 8 (70) | PAG 2 (1) | DRR 2 (10) | TEA (0.063) | PGMEA (480) | 20.0 | 0.22 | rectangular |
| II-21 | Polymer 8 (70) | PAG 2 (1) | DRR 3 (10) | TEA (0.063) | PGMEA (480) | 22.0 | 0.22 | rectangular |
| II-22 | Polymer 8 (70) | PAG 2 (1) | DRR 4 (10) | TEA (0.063) | PGMEA (480) | 22.0 | 0.20 | rectangular |
| II-22 | Polymer 8 (80) | PAG 2 (1) | ACC 1 (4) | TEA (0.063) | PGMEA (480) | 20.0 | 0.21 | rectangular |
| II-23 | Polymer 8 (80) | PAG 2 (1) | ACC 2 (4) | TEA (0.063) | PGMEA (480) | 22.0 | 0.21 | rectangular |

It is seen from Table 2 that the resist compositions within the scope of the invention have a high sensitivity and resolution upon KrF excimer laser exposure.

Example III

Resist compositions were formulated using inventive polymers and examined for resolution upon ArF excimer laser exposure.

Examples III-1 to III-2

Evaluation of Resist Resolution

Resist compositions were prepared as in Example II in accordance with the formulation shown in Table 3.

The resulting resist solutions were spin coated onto hexamethyldisilazane-spray coated silicon wafers at 90° C. for 90 seconds, then heat treated at 110° C. for 90 seconds to give resist films having a thickness of 0.5 μm. The resist films were exposed using an ArF excimer laser stepper (Nikon Corporation; NA 0.55), then heat treated at 110° C. for 90 seconds, and puddle developed with a solution of 2.38% TMAH in water for 60 seconds, thereby giving 1:1 line-and-space patterns.

The wafers as developed were sectioned and observed under sectional SEM. The optimal dose (Eop, mJ/cm$^2$) was defined as the dose which provided a 1:1 resolution at the top and bottom of a 0.25 μm line-and-space pattern. The resolution of the resist under evaluation was defined as the minimum line width (μm) of the lines and spaces that separated at the optimal dose. The shape of the resolved resist pattern was examined under a SEM.

The composition and test results of the resist materials are shown in Table 3. It is noted that the solvents and basic compounds in Table 3 are as follows. It is noted that the solvent contained 0.01% by weight of surfactant Florade FC-430 (Sumitomo 3M).
PGMEA: propylene glycol methyl ether acetate
TEA: triethanolamine
TMMEA: trismethoxymethoxyethylamine

TABLE 3

| Example | Resin (pbw) | Photoacid generator (pbw) | Basic compound (pbw) | Solvent (pbw) | Eop, mJ/cm$^2$ | Resolution, μm | Shape |
|---|---|---|---|---|---|---|---|
| III-1 | Polymer 6 (80) | PAG1 (1) | TEA (0.063) | PGMEA (480) | 17.0 | 0.16 | rectangular |
| III-2 | Polymer 6 (80) | PAG2 (1) | TMMEA (0.118) | PGMEA (480) | 18.0 | 0.15 | rectangular |

It is seen from Table 3 that the resist compositions within the scope of the invention have a high sensitivity and resolution upon ArF excimer laser exposure.

Japanese Patent Application No. 2001-008988 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An ether compound of the following general formula

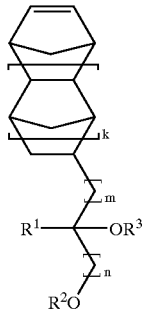

(1)

wherein $R^1$ is hydrogen or a straight, branched or cyclic alicyl group of 1 to 6 carbon atoms, $R^2$ is a straight, branched or cyclic alkyl group of 1 to 6 carbon atoms, $R^3$ is hydrogen or an acyl or alkoxycarbonyl group of 1 to 15 carbon atoms in which some or all of the hydrogen atoms on the constituent carbon atoms may be substituted with halogen atoms, k is 0 or 1, m is an integer from 0 to 3, and n is an integer from 3 to 6.

2. An ether compound according to claim 1, wherein $R^1$ is hydrogen, methyl, ethyl, n-propyl, isopropyl, n-butyl, isobutyl, sec-butyl, tert-butyl, tert-amyl, n-pentyl, n-hexyl, cyclopentyl, or cyclohexyl.

3. An ether compound according to claim 1, wherein $R^2$ is methyl, ethyl, n-propyl, isopropyl, n-butyl, isobutyl, sec-butyl, tert-butyl, tert-amyl, n-pentyl, n-hexyl, cyclopentyl, or cyclohexyl.

4. An ether compound according to claim 1 wherein $R^3$ is hydrogen, formyl, acetyl, propionyl, pivaloyl, methoxycarbonyl, proxycarbonyl, tert-butoxycarbonyl, trifluoroacetyl, trichloroacetyl, or 3,3,3,-trifluoropropionyl.

* * * * *